(12) United States Patent
Shluzas et al.

(10) Patent No.: US 11,166,751 B2
(45) Date of Patent: Nov. 9, 2021

(54) POLYAXIAL PEDICLE SCREW

(71) Applicant: Zimmer Spine, Inc., Edina, MN (US)

(72) Inventors: Alan E. Shluzas, Redwood City, CA (US); Hugh D Hestad, Edina, MN (US)

(73) Assignee: Zimmer Spine, Inc., Edina, MN (US)

( * ) Notice: Subject to any disclaimer, the term of this patent is extended or adjusted under 35 U.S.C. 154(b) by 0 days.

(21) Appl. No.: 17/248,817

(22) Filed: Feb. 9, 2021

(65) Prior Publication Data

US 2021/0161561 A1 Jun. 3, 2021

Related U.S. Application Data

(63) Continuation of application No. 16/894,991, filed on Jun. 8, 2020, now Pat. No. 10,945,766, which is a continuation of application No. 16/222,666, filed on Dec. 17, 2018, now Pat. No. 10,925,646, which is a continuation of application No. 15/469,908, filed on
(Continued)

(51) Int. Cl.
*A61B 17/68* (2006.01)
*A61B 17/70* (2006.01)
*A61B 17/00* (2006.01)

(52) U.S. Cl.
CPC ............. *A61B 17/68* (2013.01); *A61B 17/70* (2013.01); *A61B 17/7001* (2013.01); *A61B 17/7032* (2013.01); *A61B 17/7035* (2013.01); *A61B 17/7037* (2013.01); *A61B 2017/00526* (2013.01)

(58) Field of Classification Search
CPC ..... A61B 17/68; A61B 17/70; A61B 17/7001; A61B 17/7032; A61B 17/7035; A61B 17/7037; A61B 2017/00526
See application file for complete search history.

(56) References Cited

U.S. PATENT DOCUMENTS 1,474,050 A 11/1923 Mccurdy
2,173,104 A 9/1939 Fuller
(Continued)

FOREIGN PATENT DOCUMENTS

DE 19507141 A1 9/1996
EP 1121902 B1 9/2004
(Continued)

OTHER PUBLICATIONS

"U.S. Appl. No. 13/778,684, Non Final Office Action dated Apr. 22, 2015", 10 pgs.
(Continued)

*Primary Examiner* — Pedro Philogene
(74) *Attorney, Agent, or Firm* — Schwegman Lundberg & Woessner, P.A.

(57) ABSTRACT

A polyaxial bone anchor including a housing, a bone screw, and a retainer for pivotably coupling the head of the bone screw to the housing. The retainer is positioned into the bore of the housing and includes a plurality of alternating tabs and slots circumferentially arranged to define a cavity for receiving the head portion of the bone screw therein. The retainer is axially moveable in the housing from a first position in which the head portion is not passable through the lower opening of the retainer to a second position in which lie head portion is passable through the lower opening of the retainer.

21 Claims, 16 Drawing Sheets

Related U.S. Application Data

Mar. 27, 2017, now Pat. No. 10,182,844, which is a continuation of application No. 14/924,521, filed on Oct. 27, 2015, now Pat. No. 9,636,148, which is a continuation of application No. 13/778,684, filed on Feb. 27, 2013, now Pat. No. 9,198,695, which is a continuation of application No. PCT/US2011/049533, filed on Aug. 29, 2011.

(60) Provisional application No. 61/378,182, filed on Aug. 30, 2010.

(56) References Cited

U.S. PATENT DOCUMENTS

| | | |
|---|---|---|
| 3,433,510 A | 3/1969 | Hulterstrum |
| 4,273,116 A | 6/1981 | Chiquet |
| 4,419,026 A | 12/1983 | Leto |
| 4,483,334 A | 11/1984 | Murray |
| 4,570,982 A | 2/1986 | Blose et al. |
| 4,693,240 A | 9/1987 | Evans |
| 4,708,510 A | 11/1987 | Mcconnell et al. |
| 4,763,644 A | 8/1988 | Webb |
| 4,805,602 A | 2/1989 | Puno et al. |
| 4,836,196 A | 6/1989 | Park et al. |
| 4,841,959 A | 6/1989 | Ransford |
| 4,854,304 A | 8/1989 | Zielke |
| 4,867,144 A | 9/1989 | Karas et al. |
| 4,887,595 A | 12/1989 | Heinig et al. |
| 4,887,596 A | 12/1989 | Sherman |
| 4,946,458 A | 8/1990 | Harms et al. |
| 5,002,542 A | 3/1991 | Frigg |
| 5,005,562 A | 4/1991 | Cotrel |
| 5,084,049 A | 1/1992 | Asher et al. |
| 5,085,660 A | 2/1992 | Lin |
| 5,092,893 A | 3/1992 | Smith |
| 5,129,388 A | 7/1992 | Vignaud et al. |
| 5,129,900 A | 7/1992 | Asher et al. |
| 5,133,716 A | 7/1992 | Plaza |
| 5,133,717 A | 7/1992 | Chopin |
| 5,176,678 A | 1/1993 | Tsou |
| 5,261,909 A | 11/1993 | Sutterlin et al. |
| 5,261,912 A | 11/1993 | Frigg |
| 5,312,404 A | 5/1994 | Asher et al. |
| 5,312,405 A | 5/1994 | Korotko et al. |
| 5,330,477 A | 7/1994 | Crook |
| 5,364,399 A | 11/1994 | Lowery et al. |
| 5,395,371 A | 3/1995 | Miller et al. |
| 5,429,639 A | 7/1995 | Judet |
| 5,437,671 A | 8/1995 | Lozier et al. |
| 5,466,237 A | 11/1995 | Byrd, III et al. |
| 5,470,333 A | 11/1995 | Ray |
| 5,474,555 A | 12/1995 | Puno et al. |
| 5,476,462 A | 12/1995 | Allard et al. |
| 5,498,262 A | 3/1996 | Bryan |
| 5,498,263 A | 3/1996 | Dinello et al. |
| 5,501,684 A | 3/1996 | Schlapfer et al. |
| 5,527,314 A | 6/1996 | Brumfield et al. |
| 5,531,746 A | 7/1996 | Errico et al. |
| 5,545,164 A | 8/1996 | Howland |
| 5,549,608 A | 8/1996 | Errico et al. |
| 5,562,661 A | 10/1996 | Yoshimi et al. |
| 5,569,247 A | 10/1996 | Morrison |
| 5,575,792 A | 11/1996 | Errico et al. |
| 5,578,033 A | 11/1996 | Errico et al. |
| 5,584,834 A | 12/1996 | Errico et al. |
| 5,591,165 A | 1/1997 | Jackson |
| 5,591,166 A | 1/1997 | Bernhardt et al. |
| 5,601,552 A | 2/1997 | Cotrel |
| 5,601,553 A | 2/1997 | Trebing et al. |
| 5,609,593 A | 3/1997 | Errico et al. |
| 5,609,594 A | 3/1997 | Errico et al. |
| 5,628,740 A | 5/1997 | Mullane |
| 5,647,873 A | 7/1997 | Errico et al. |
| 5,669,910 A | 9/1997 | Korhonen et al. |
| 5,681,319 A | 10/1997 | Biedermann et al. |
| 5,688,272 A | 11/1997 | Montague et al. |
| 5,688,273 A | 11/1997 | Errico et al. |
| 5,716,355 A | 2/1998 | Jackson et al. |
| 5,716,356 A | 2/1998 | Biedermann et al. |
| 5,716,357 A | 2/1998 | Rogozinski |
| 5,725,528 A | 3/1998 | Errico et al. |
| 5,725,588 A | 3/1998 | Errico et al. |
| 5,728,098 A | 3/1998 | Sherman et al. |
| 5,733,286 A | 3/1998 | Errico et al. |
| 5,738,685 A | 4/1998 | Halm et al. |
| 5,782,833 A | 7/1998 | Haider |
| 5,810,818 A | 9/1998 | Errico et al. |
| 5,873,878 A | 2/1999 | Harms et al. |
| 5,876,402 A | 3/1999 | Errico et al. |
| 5,879,350 A | 3/1999 | Sherman et al. |
| 5,879,351 A | 3/1999 | Viart |
| 5,885,286 A | 3/1999 | Sherman et al. |
| 5,891,145 A | 4/1999 | Morrison et al. |
| 5,902,303 A | 5/1999 | Eckhof et al. |
| 5,947,966 A | 9/1999 | Drewry et al. |
| 5,954,725 A | 9/1999 | Sherman et al. |
| 5,961,517 A | 10/1999 | Biedermann et al. |
| 5,980,523 A | 11/1999 | Jackson |
| 6,010,503 A | 1/2000 | Richelsoph et al. |
| 6,015,409 A | 1/2000 | Jackson |
| 6,022,350 A | 2/2000 | Ganem |
| 6,050,997 A | 4/2000 | Mullane |
| 6,053,917 A | 4/2000 | Sherman et al. |
| 6,063,090 A | 5/2000 | Schlapfer |
| 6,074,391 A | 6/2000 | Metz-stavenhagen et al. |
| 6,077,262 A | 6/2000 | Schlapfer et al. |
| 6,080,156 A | 6/2000 | Asher et al. |
| 6,086,588 A | 7/2000 | Ameil et al. |
| 6,090,110 A | 7/2000 | Metz-stavenhagen |
| 6,090,111 A | 7/2000 | Nichols |
| 6,099,528 A | 8/2000 | Saurat |
| 6,110,172 A | 8/2000 | Jackson |
| 6,113,600 A | 9/2000 | Drummond et al. |
| RE37,161 E | 5/2001 | Michelson et al. |
| 6,261,287 B1 | 7/2001 | Metz-stavenhagen |
| 6,296,642 B1 | 10/2001 | Morrison et al. |
| 6,302,888 B1 | 10/2001 | Mellinger et al. |
| 6,309,391 B1 | 10/2001 | Crandall et al. |
| 6,331,179 B1 | 12/2001 | Freid et al. |
| 6,355,040 B1 | 3/2002 | Richelsoph et al. |
| RE37,665 E | 4/2002 | Ralph et al. |
| 6,367,321 B1 | 4/2002 | Miyairi |
| 6,382,436 B1 | 5/2002 | Wang |
| 6,402,752 B2 | 6/2002 | Schäffler-Wachter et al. |
| 6,436,100 B1 | 8/2002 | Berger |
| 6,440,137 B1 | 8/2002 | Horvath et al. |
| 6,451,021 B1 | 9/2002 | Ralph et al. |
| 6,471,703 B1 | 10/2002 | Ashman |
| 6,471,705 B1 | 10/2002 | Biedermann et al. |
| 6,485,491 B1 | 11/2002 | Farris et al. |
| 6,533,786 B1 | 3/2003 | Needham et al. |
| 6,537,276 B2 | 3/2003 | Metz-Stavenhagen |
| 6,547,789 B1 | 4/2003 | Ventre et al. |
| 6,547,790 B2 | 4/2003 | Harkey, III et al. |
| 6,551,320 B2 | 4/2003 | Lieberman |
| 6,554,832 B2 | 4/2003 | Shluzas |
| 6,554,834 B1 | 4/2003 | Crozet et al. |
| 6,562,040 B1 | 5/2003 | Wagner |
| 6,565,567 B1 | 5/2003 | Haider |
| 6,582,436 B2 | 6/2003 | Schlapfer et al. |
| 6,582,466 B1 | 6/2003 | Gauchet |
| 6,585,740 B2 | 7/2003 | Schlapfer et al. |
| 6,595,992 B1 | 7/2003 | Wagner et al. |
| 6,595,993 B2 | 7/2003 | Donno et al. |
| 6,610,063 B2 | 8/2003 | Kumar et al. |
| 6,613,050 B1 | 9/2003 | Wagner et al. |
| 6,623,485 B2 | 9/2003 | Doubler |
| 6,626,907 B2 | 9/2003 | Campbell et al. |
| 6,626,908 B2 | 9/2003 | Cooper et al. |
| 6,635,059 B2 | 10/2003 | Randall et al. |
| 6,648,885 B1 | 11/2003 | Friesem |
| 6,648,887 B2 | 11/2003 | Ashman |
| 6,656,179 B1 | 12/2003 | Schaefer et al. |

(56) References Cited

U.S. PATENT DOCUMENTS

| | | |
|---|---|---|
| 6,656,181 B2 | 12/2003 | Dixon et al. |
| 6,660,004 B2 | 12/2003 | Barker et al. |
| 6,663,632 B1 | 12/2003 | Frigg |
| 6,663,635 B2 | 12/2003 | Frigg et al. |
| 6,672,788 B2 | 1/2004 | Hathaway |
| 6,673,073 B1 | 1/2004 | Schäfer |
| 6,676,661 B1 | 1/2004 | Martin Benlloch et al. |
| 6,679,833 B2 | 1/2004 | Smith et al. |
| 6,682,529 B2 | 1/2004 | Stahurski |
| 6,689,133 B2 | 2/2004 | Morrison et al. |
| 6,689,134 B2 | 2/2004 | Ralph et al. |
| 6,695,843 B2 | 2/2004 | Biedermann et al. |
| 6,695,851 B2 | 2/2004 | Zdeblick et al. |
| 6,699,249 B2 | 3/2004 | Schlapfer et al. |
| 6,706,045 B2 | 3/2004 | Lin |
| 6,712,818 B1 | 3/2004 | Michelson |
| 6,716,213 B2 | 4/2004 | Shitoto |
| 6,716,214 B1 | 4/2004 | Jackson |
| 6,716,247 B2 | 4/2004 | Michelson |
| 6,723,100 B2 | 4/2004 | Biedermann et al. |
| 6,726,689 B2 | 4/2004 | Jackson |
| 6,730,093 B2 | 5/2004 | Saint Martin |
| 6,730,127 B2 | 5/2004 | Michelson |
| 6,733,502 B2 | 5/2004 | Altarac et al. |
| 6,736,816 B2 | 5/2004 | Ritland |
| 6,736,820 B2 | 5/2004 | Biedermann et al. |
| 6,740,086 B2 | 5/2004 | Richelsoph |
| 6,746,449 B2 | 6/2004 | Jones et al. |
| 6,755,829 B1 | 6/2004 | Bono et al. |
| 6,755,835 B2 | 6/2004 | Schultheiss et al. |
| 6,755,836 B1 | 6/2004 | Lewis |
| 6,761,723 B2 | 7/2004 | Buttermann et al. |
| 6,767,351 B2 | 7/2004 | Orbay et al. |
| 6,770,075 B2 | 8/2004 | Howland |
| 6,780,186 B2 | 8/2004 | Errico et al. |
| 6,790,209 B2 | 9/2004 | Beale et al. |
| 6,827,719 B2 | 12/2004 | Ralph et al. |
| 6,830,571 B2 | 12/2004 | Lenke |
| 6,835,196 B2 | 12/2004 | Biedermann et al. |
| 6,837,889 B2 | 1/2005 | Shluzas |
| 6,840,940 B2 | 1/2005 | Ralph et al. |
| 6,843,791 B2 | 1/2005 | Serhan |
| 6,858,031 B2 | 2/2005 | Morrison et al. |
| 6,869,432 B2 | 3/2005 | Schlapfer et al. |
| 6,869,433 B2 | 3/2005 | Glascott |
| 6,872,208 B1 | 3/2005 | Mcbride et al. |
| 6,932,817 B2 | 8/2005 | Baynham et al. |
| 6,945,972 B2 | 9/2005 | Frigg et al. |
| 6,950,997 B2 | 9/2005 | Dickey et al. |
| 6,953,462 B2 | 10/2005 | Lieberman |
| 6,955,677 B2 | 10/2005 | Dahners |
| 6,958,065 B2 | 10/2005 | Ueyama et al. |
| 6,964,664 B2 | 11/2005 | Freid et al. |
| 6,964,665 B2 | 11/2005 | Thomas et al. |
| 6,974,460 B2 | 12/2005 | Carbone et al. |
| 6,979,334 B2 | 12/2005 | Dalton |
| 6,981,973 B2 | 1/2006 | Mckinley |
| RE39,035 E | 3/2006 | Finn et al. |
| 7,018,378 B2 | 3/2006 | Biedermann et al. |
| 7,018,379 B2 | 3/2006 | Drewry et al. |
| 7,066,937 B2 | 6/2006 | Shluzas |
| 7,128,743 B2 | 10/2006 | Metz-Stavenhagen |
| 7,144,396 B2 | 12/2006 | Shluzas |
| 7,445,627 B2 | 11/2008 | Hawkes et al. |
| 7,604,656 B2 | 10/2009 | Shluzas |
| 7,682,377 B2 | 3/2010 | Konieczynski et al. |
| 7,699,876 B2 * | 4/2010 | Barry ............... A61B 17/7037 606/266 |
| 7,789,900 B2 | 9/2010 | Levy et al. |
| 8,021,397 B2 | 9/2011 | Farris et al. |
| 8,192,470 B2 | 6/2012 | Biedermann et al. |
| 8,197,517 B1 | 6/2012 | Lab et al. |
| 8,308,782 B2 | 11/2012 | Jackson |
| 8,663,298 B2 | 3/2014 | Keyer et al. |
| 8,696,712 B2 | 4/2014 | Biedermann et al. |
| 8,882,817 B2 * | 11/2014 | Jones ............... A61B 17/7037 606/305 |
| 9,198,695 B2 | 12/2015 | Shluzas et al. |
| 9,486,246 B2 | 11/2016 | Matthis et al. |
| 9,636,148 B2 | 5/2017 | Shluzas |
| 10,182,844 B2 | 1/2019 | Shluzas et al. |
| 10,925,646 B2 | 2/2021 | Shluzas et al. |
| 2001/0001119 A1 | 5/2001 | Lombardo |
| 2002/0035366 A1 | 3/2002 | Walder et al. |
| 2002/0045898 A1 | 4/2002 | Freid et al. |
| 2002/0082602 A1 | 6/2002 | Biedermann et al. |
| 2002/0103487 A1 | 8/2002 | Errico et al. |
| 2002/0111626 A1 | 8/2002 | Ralph et al. |
| 2002/0143341 A1 | 10/2002 | Biedermann et al. |
| 2002/0173789 A1 | 11/2002 | Howland |
| 2002/0193795 A1 | 12/2002 | Gertzbein et al. |
| 2003/0004512 A1 | 1/2003 | Farris et al. |
| 2003/0023243 A1 | 1/2003 | Biedermann et al. |
| 2003/0045879 A1 | 3/2003 | Minfelde et al. |
| 2003/0073996 A1 | 4/2003 | Doubler et al. |
| 2003/0093078 A1 | 5/2003 | Ritland |
| 2003/0105460 A1 | 6/2003 | Crandall et al. |
| 2003/0118395 A1 | 6/2003 | Abels et al. |
| 2003/0125741 A1 | 7/2003 | Biedermann et al. |
| 2003/0149432 A1 | 8/2003 | Frigg et al. |
| 2003/0163133 A1 | 8/2003 | Altarac et al. |
| 2003/0176862 A1 | 9/2003 | Taylor et al. |
| 2003/0199873 A1 | 10/2003 | Richelsoph |
| 2003/0208204 A1 | 11/2003 | Bailey et al. |
| 2003/0216735 A1 | 11/2003 | Altarac et al. |
| 2004/0006342 A1 | 1/2004 | Altarac et al. |
| 2004/0024464 A1 | 2/2004 | Errico et al. |
| 2004/0092934 A1 | 5/2004 | Howland |
| 2004/0097933 A1 | 5/2004 | Lourdel et al. |
| 2004/0102781 A1 | 5/2004 | Jeon |
| 2004/0127906 A1 | 7/2004 | Culbert et al. |
| 2004/0138662 A1 | 7/2004 | Landry et al. |
| 2004/0143265 A1 | 7/2004 | Landry et al. |
| 2004/0147929 A1 | 7/2004 | Biedermann et al. |
| 2004/0158247 A1 | 8/2004 | Sitiso et al. |
| 2004/0181224 A1 | 9/2004 | Biedermann et al. |
| 2005/0033289 A1 | 2/2005 | Warren et al. |
| 2005/0131409 A1 | 6/2005 | Chervitz et al. |
| 2005/0131537 A1 | 6/2005 | Hoy et al. |
| 2005/0131538 A1 | 6/2005 | Chervitz et al. |
| 2005/0131545 A1 | 6/2005 | Chervitz et al. |
| 2005/0192571 A1 | 9/2005 | Abdelgany |
| 2005/0203515 A1 | 9/2005 | Doherty et al. |
| 2005/0228392 A1 | 10/2005 | Keyer et al. |
| 2005/0261687 A1 | 11/2005 | Garamszegi et al. |
| 2006/0004359 A1 | 1/2006 | Kramer et al. |
| 2006/0009769 A1 | 1/2006 | Lieberman |
| 2006/0009770 A1 | 1/2006 | Speirs et al. |
| 2006/0015104 A1 | 1/2006 | Dalton |
| 2006/0015105 A1 | 1/2006 | Warren et al. |
| 2006/0025767 A1 | 2/2006 | Khalili |
| 2006/0025768 A1 | 2/2006 | Iott et al. |
| 2006/0025770 A1 | 2/2006 | Schlapfer et al. |
| 2006/0036242 A1 | 2/2006 | Nilsson et al. |
| 2006/0036252 A1 | 2/2006 | Baynham et al. |
| 2006/0052783 A1 | 3/2006 | Dant et al. |
| 2006/0052784 A1 | 3/2006 | Dant et al. |
| 2006/0052786 A1 | 3/2006 | Dant et al. |
| 2006/0058788 A1 | 3/2006 | Hammer et al. |
| 2006/0084981 A1 | 4/2006 | Shluzas |
| 2006/0149240 A1 | 7/2006 | Jackson |
| 2006/0149241 A1 | 7/2006 | Richelsoph et al. |
| 2006/0155277 A1 | 7/2006 | Metz-stavenhagen |
| 2006/0235392 A1 | 10/2006 | Hammer et al. |
| 2006/0241599 A1 | 10/2006 | Konieczynski et al. |
| 2006/0241603 A1 | 10/2006 | Jackson |
| 2006/0276791 A1 | 12/2006 | Shluzas |
| 2006/0293665 A1 | 12/2006 | Shluzas |
| 2007/0055241 A1 | 3/2007 | Matthis et al. |
| 2007/0093818 A1 | 4/2007 | Biedermann et al. |
| 2007/0093826 A1 | 4/2007 | Hawkes et al. |
| 2007/0118132 A1 | 5/2007 | Culbert et al. |
| 2007/0123868 A1 | 5/2007 | Culbert et al. |
| 2007/0161996 A1 | 7/2007 | Biedermann et al. |

(56) References Cited

U.S. PATENT DOCUMENTS

| | | |
|---|---|---|
| 2007/0161999 A1 | 7/2007 | Biedermann et al. |
| 2007/0219556 A1 | 9/2007 | Altarac et al. |
| 2007/0225712 A1 | 9/2007 | Altarac et al. |
| 2007/0225713 A1 | 9/2007 | Altarac et al. |
| 2007/0270813 A1 | 11/2007 | Garamszegi |
| 2007/0288004 A1 | 12/2007 | Alvarez |
| 2008/0009862 A1 | 1/2008 | Hoffman |
| 2008/0015576 A1 | 1/2008 | Whipple |
| 2008/0015579 A1 | 1/2008 | Whipple |
| 2008/0015580 A1 | 1/2008 | Chao |
| 2008/0015597 A1 | 1/2008 | Whipple |
| 2008/0045953 A1 | 2/2008 | Garamszegi |
| 2008/0097436 A1 | 4/2008 | Culbert et al. |
| 2008/0177322 A1 | 7/2008 | Davis et al. |
| 2008/0269809 A1 | 10/2008 | Garamszegi |
| 2008/0287998 A1 | 11/2008 | Doubler et al. |
| 2009/0163956 A1 | 6/2009 | Biedermann et al. |
| 2010/0137920 A1 | 6/2010 | Hammill, Sr. et al. |
| 2010/0262196 A1 | 10/2010 | Barrus et al. |
| 2011/0040336 A1* | 2/2011 | Hammill, Sr. ..... A61B 17/7037 606/305 |
| 2013/0150852 A1 | 6/2013 | Shluzas et al. |
| 2016/0045229 A1 | 2/2016 | Shluzas et al. |
| 2017/0196595 A1 | 7/2017 | Shluzas et al. |
| 2019/0110817 A1 | 4/2019 | Shluzas et al. |
| 2020/0297389 A1 | 9/2020 | Shluzas et al. |

FOREIGN PATENT DOCUMENTS

| | | |
|---|---|---|
| EP | 1579816 A1 | 9/2005 |
| EP | 1634537 B1 | 11/2007 |
| EP | 1190678 B1 | 6/2008 |
| EP | 1570795 B1 | 8/2008 |
| FR | 2729291 A1 | 7/1996 |
| FR | 2796545 A1 | 1/2001 |
| FR | 2856578 A1 | 12/2004 |
| FR | 2857850 A1 | 1/2005 |
| FR | 2865373 A1 | 7/2005 |
| FR | 2865375 A1 | 7/2005 |
| FR | 2865378 A1 | 7/2005 |
| GB | 2365345 A | 2/2002 |
| WO | WO-9825534 A1 | 6/1998 |
| WO | WO-03068083 A1 | 8/2003 |
| WO | WO-2004041100 A1 | 5/2004 |
| WO | WO-2004089245 A2 | 10/2004 |
| WO | WO-2004107997 A2 | 12/2004 |
| WO | WO-2005000136 A1 | 1/2005 |
| WO | WO-2005000137 A1 | 1/2005 |
| WO | WO-2005020829 A1 | 3/2005 |
| WO | WO-2005072632 A1 | 8/2005 |
| WO | WO-2005082262 A2 | 9/2005 |
| WO | WO-2005099400 A2 | 10/2005 |
| WO | WO-2006012088 A1 | 2/2006 |
| WO | WO-2006017616 A1 | 2/2006 |
| WO | WO-2006028537 A2 | 3/2006 |
| WO | WO-2009014540 A1 | 1/2009 |
| WO | WO-2010056846 A2 | 5/2010 |
| WO | WO-2012030712 A1 | 3/2012 |

OTHER PUBLICATIONS

"U.S. Appl. No. 13/778,684, Notice of Allowance dated Jul. 28, 2015", 8 pgs.

"U.S. Appl. No. 13/778,684, Response filed Jun. 16, 2015 to Non Final Office Action dated Apr. 22, 2015", 9 pgs.

"U.S. Appl. No. 13/778,684, Response filed Sep. 24, 2013 to Restriction Requirement dated Sep. 17, 2013", 7 pgs.

"U.S. Appl. No. 13/778,684, Restriction Requirement dated Sep. 17, 2013", 9 pgs.

"U.S. Appl. No. 14/924,521, Non Final Office Action dated Sep. 1, 2016", 7 pgs.

"U.S. Appl. No. 14/924,521, Notice of Allowance dated Dec. 27, 2016", 7 pgs.

"U.S. Appl. No. 14/924,521, Preliminary Amendment filed Nov. 19, 2015", 6 pgs.

"U.S. Appl. No. 14/924,521, Response filed Nov. 14, 2016 to Non Final Office Action dated Sep. 1, 2006", 8 pgs.

"U.S. Appl. No. 15/469,908, Non Final Office Action dated May 16, 2018", 11 pgs.

"U.S. Appl. No. 15/469,908, Notice of Allowance dated Sep. 24, 2018", 5 pgs.

"U.S. Appl. No. 15/469,908, Preliminary Amendment filed Apr. 12, 2017", 7 pgs.

"U.S. Appl. No. 15/469,908, Response filed Jul. 12, 2018 to Non Final Office Action dated May 16, 2018", 18 pgs.

"U.S. Appl. No. 16/222,666, Corrected Notice of Allowability dated Dec. 1, 2020", 5 pgs.

"U.S. Appl. No. 16/222,666, Final Office Action dated Aug. 10, 2020", 13 pgs.

"U.S. Appl. No. 16/222,666, Non Final Office Action dated Apr. 10, 2020", 14 pgs.

"U.S. Appl. No. 16/222,666, Notice of Allowance dated Oct. 22, 2020", 5 pgs.

"U.S. Appl. No. 16/222,666, Preliminary Amendment filed Jan. 7, 2019", 9 pgs.

"U.S. Appl. No. 16/222,666, Response filed Jul. 10, 20 to Non Final Office Action dated Apr. 10, 2020", 18 pgs.

"U.S. Appl. No. 16/222,666, Response filed Oct. 12, 2020 to Final Office Action dated Aug. 10, 2020", 18 pgs.

"U.S. Appl. No. 16/894,991, Examiner Interview Summary dated Sep. 9, 2020", 3 pages.

"U.S. Appl. No. 16/894,991, Non Final Office Action dated Jul. 2, 2020", 9 pgs.

"U.S. Appl. No. 16/894,991, Notice of Allowance dated Nov. 10, 2020", 5 pgs.

"U.S. Appl. No. 16/894,991, Preliminary Amendment filed Jun. 9, 2020", 7 pgs.

"U.S. Appl. No. 16/894,991, Response filed Sep. 30, 2020 to Non Final Office Action dated Jul. 2, 2020", 18 pgs.

"European Application Serial No. 11758601.6, Decision to Grant dated Oct. 8, 2015", 2 pgs.

"European Application Serial No. 11758601.6, Examination Notification Art. 94(3) dated Oct. 17, 2014", 5 pgs.

"European Application Serial No. 11758601.6, Office Action dated May 12, 2015", 6 pgs.

"European Application Serial No. 11758601.6, Response filed Feb. 26, 2015 to Examination Notification Art. 94(3) dated Oct. 17, 2014", 10 pgs.

"International Application Serial No. PCT/US2011/049533, International Preliminary Report on Patentability dated Mar. 14, 2013", 16 pgs.

"International Application Serial No. PCT/US2011/049533, International Search Report dated Jan. 25, 2012", 7 pgs.

"International Application Serial No. PCT/US2011/049533, Written Opinion dated Jan. 25, 2012", 14 pgs.

\* cited by examiner

POLYAXIAL PEDICLE SCREW

CROSS-REFERENCE TO RELATED APPLICATIONS

This application is a continuation of Ser. No. 16/894,991, filed on Jun. 8, 2020, which is a continuation of Ser. No. 16/222,666, filed on Dec. 17, 2018, which is a continuation of Ser. No. 15/469,908, filed on Mar. 27, 2017, which is a continuation of Ser. No. 14/924,521, filed on Oct. 27, 2015, which is a continuation of Ser. No. 13/778,684, filed on Feb. 27, 2013, which is a continuation of PCT/US2011/049533, filed on Aug. 29, 2011, which claims priority to U.S. Provisional Application 61/378,182, filed on Aug. 30, 2010, the entire disclosure of which are incorporated herein by reference.

TECHNICAL FIELD

The disclosure is directed to vertebral anchors for use with orthopedic fixation systems. More particularly, the disclosure is directed to polyaxial pedicle screws including structures for securely coupling a bone screw to a housing of the polyaxial pedicle screw.

BACKGROUND

The spinal column of a patient includes a plurality of vertebrae linked to one another by facet joints and an intervertebral disc located between adjacent vertebrae. The facet joints and intervertebral disc allow one vertebra to move relative to an adjacent vertebra, providing the spinal column a range of motion. Diseased, degenerated, damaged, or otherwise impaired facet joints and/or intervertebral discs may cause the patient to experience pain or discomfort and/or loss of motion, thus prompting surgery to alleviate the pain and/or restore motion of the spinal column.

One possible method of treating these conditions is to immobilize a portion of the spine to allow treatment. Traditionally, immobilization has been accomplished by rigid stabilization. For example, in a conventional spinal fusion procedure, a surgeon restores the alignment of the spine or the disc space between vertebrae by installing a rigid fixation rod between pedicle screws secured to adjacent vertebrae. Bone graft is placed between the vertebrae, and the fixation rod cooperates with the screws to immobilize the two vertebrae relative to each other so that the bone graft may fuse with the vertebrae.

Dynamic stabilization has also been used in spinal treatment procedures. Dynamic stabilization does not result in complete immobilization, but instead permits a degree of mobility of the spine while also providing sufficient support and stabilization to effect treatment. One example of a dynamic stabilization system is the Dynesys® system available from Zimmer Spine, Inc. of Minneapolis, Minn. Such dynamic stabilization systems typically include a flexible member positioned between pedicle screws installed in adjacent vertebrae of the spine. A flexible cord can be threaded through the bore in the flexible member and secured to the pedicle screws while cooperating with the flexible member to permit mobility of the spine.

Thus, it may be desirable to provide alternative vertebral anchors which may be used in spinal stabilization systems which are configured to secure elongate members or other structures to one or more vertebrae of a spinal segment of a spinal column in a desired configuration in treating various spinal disorders.

Accordingly, it is desirable to develop a pedicle screw that provides polyaxial rotation which is easily assembled and configured to be secured in a desired angular orientation when secured to an elongated member of a vertebral stabilization system.

SUMMARY

The disclosure is directed to several alternative designs, materials and methods of assembling vertebral anchor structures and assemblies.

Accordingly, one illustrative embodiment is a polyaxial bone anchor. The polyaxial bone anchor includes a housing having an upper end, a lower end and a bore extending through the housing from the upper end to the lower end. The bore opens out at the lower end at a lower opening. The housing also includes a channel configured for receiving an elongate stabilization member therethrough which extends from a first side surface of the housing to a second side surface of the housing opposite the first side surface transverse to the bore. The bone anchor also includes a retainer positioned into the bore of the housing which has an outermost diameter greater than a diameter of the lower opening. The retainer includes a plurality of alternating tabs and slots circumferentially arranged to define a cavity therein. Also included is a bone screw including a head portion and a shank extending from the head portion. The head portion of the bone screw is positionable in the cavity of the retainer with the shank extending from the lower end of the housing by deflecting the tabs radially outward to enlarge a lower opening of the retainer into the cavity from a diameter less than a diameter of the head portion to a diameter greater than or equal to the diameter of the head portion. The bone anchor also includes means for applying a force to move the retainer toward the lower end of the housing while the retainer is positioned in the bore.

Another illustrative embodiment is a polyaxial bone anchor. The bone anchor includes a housing having an upper end, a lower end and a bore extending through the housing from the upper end to the lower end. The bore opens out at the lower end at a lower opening. The housing also includes a channel configured for receiving an elongate stabilization member therethrough which extends from a first side surface of the housing to a second side surface of the housing opposite the first side surface transverse to the bore. The bone anchor also includes a retainer positionable in the bore of the housing. The retainer is movable in the bore of the housing between a first position and a second position. The retainer is closer to the lower end of the housing in the first position and closer to the upper end of the housing in the second position. Additionally, the bone anchor includes a bone screw including a head portion and a shank extending from the head portion. The head portion of the bone screw is positionable in a cavity of the retainer with the shank extending from the lower end of the housing. The head portion of the bone screw is insertable into the cavity of the retainer from the lower end of the housing when the retainer is in the second position, but is not removable from the cavity of the retainer when the retainer is in the first position.

Another illustrative embodiment is a polyaxial bone anchor including a housing, a bone screw, a spacer, a collar and a resilient spring means. The housing has an upper end, a lower end and a bore extending through the housing from the upper end to the lower end. A lower portion of the housing includes a plurality of deflectable tabs arranged around a perimeter of the housing. The housing includes a channel configured for receiving an elongate stabilization member therethrough which extends from a first side surface of the housing to a second side surface of the housing opposite the first side surface transverse to the bore. The spacer is positionable in the bore of the housing and movable in the bore of the housing between a first position and a second position. The spacer is closer to the lower end of the housing in the first position and closer to the upper end of the housing in the second position. The bone screw includes a head portion and a shank extending from the head portion. The head portion of the bone screw is positionable in a cavity of the spacer with the shank extending from the lower end of the housing. The collar is positionable circumferentially exterior of the plurality of deflectable tabs to inhibit outward radial deflection of the plurality of tabs. The resilient spring means biases the spacer toward the first position into engagement with the head portion of the bone screw. The head portion of the bone screw is insertable into the bore of the housing from the lower end of the housing by deflecting the plurality of tabs radially outward, but is not removable from the housing when the collar is positioned circumferentially exterior of the plurality of deflectable tabs.

Yet another illustrative embodiment is a method of assembling a polyaxial bone anchor. A housing is provided having an upper end, a lower end and a bore extending through the housing from the upper end to the lower end. The bore opens out at the lower end at a lower opening. The housing also includes a channel configured for receiving an elongate stabilization member therethrough which extends from a first side surface of the housing to a second side surface of the housing opposite the first side surface transverse to the bore. A retainer is inserted into the bore of the housing from the lower end of the housing by passing the retainer through the lower opening. The retainer has an outermost diameter greater than a diameter of the lower opening. The retainer includes a plurality of alternating tabs and slots formed therein providing the retainer with sufficient flexibility to be urged through the lower opening from the lower end of the housing by radially compressing the retainer. A head portion of a bone screw is inserted into a cavity of the retainer from the lower end of the housing by moving the retainer toward the upper end of the housing allowing the plurality of tabs to splay radially outward to accommodate passage of the head portion of the bone screw into the cavity of the retainer. The retainer, with the head portion of the bone screw positioned in the cavity of the retainer, is urged back toward the lower end of the housing to retain the head portion of the bone screw in the cavity of the retainer. The retainer is biased toward the lower end of the housing by a biasing spring means.

The above summary of some example embodiments is not intended to describe each disclosed embodiment or every implementation of the invention.

BRIEF DESCRIPTION OF THE DRAWINGS

The invention may be more completely understood in consideration of the following detailed description of various embodiments in connection with the accompanying drawings, in which.

Figure 1:
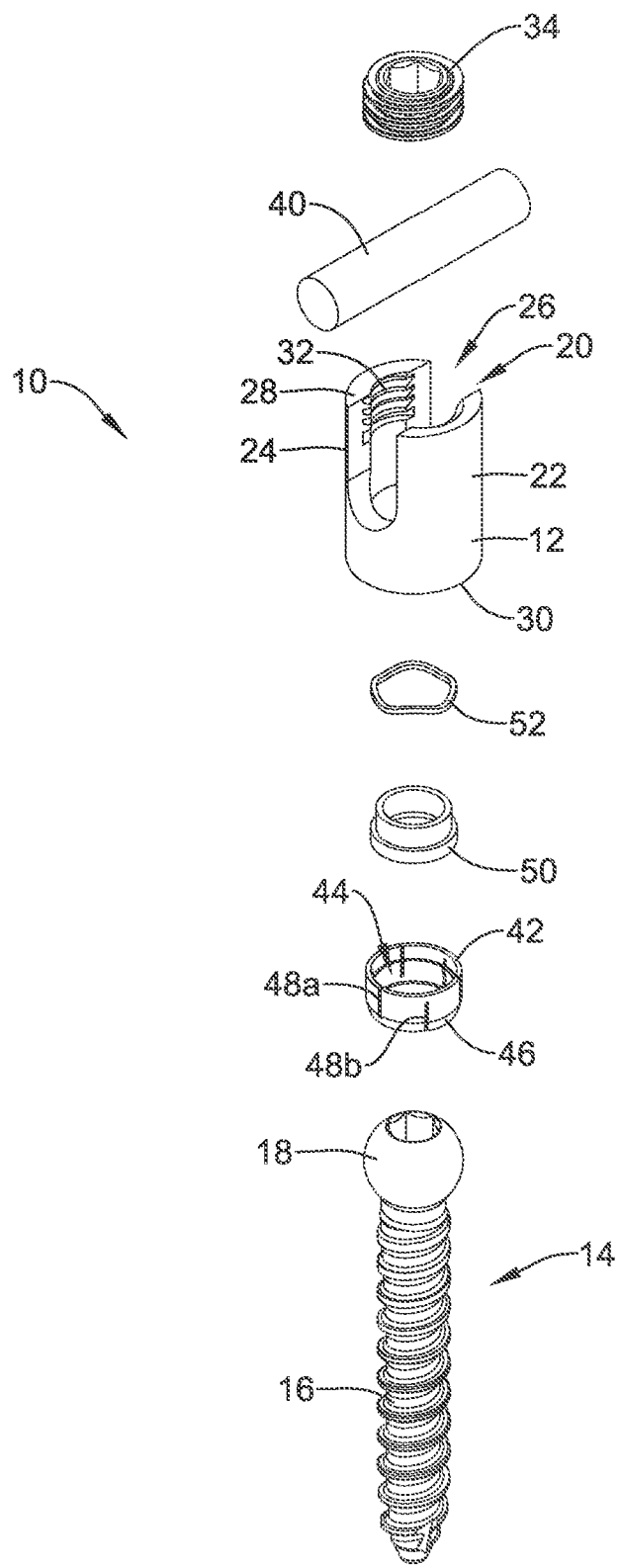
FIG. 1 is an exploded perspective view of components of an exemplary vertebral anchor.

While the invention is amenable to various modifications and alternative forms, specifics thereof have been shown by way of example in the drawings and will be described in detail. It should be understood, however, that the intention is not to limit aspects of the invention to the particular embodiments described. On the contrary, the intention is to cover all modifications, equivalents, and alternatives falling within the spirit and scope of the invention.

DETAILED DESCRIPTION

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (i.e., having the same function or result). In many instances, the term "about" may be indicative as including numbers that are rounded to the nearest significant figure.

The recitation of numerical ranges by endpoints includes all numbers within that range (e.g., 1 to 5 includes 1, 1.5, 2, 2.75, 3, 3.80, 4, and 5).

Although some suitable dimensions, ranges and/or values pertaining to various components, features and/or specifications are disclosed, one of skill in the art, incited by the present disclosure, would understand desired dimensions, ranges and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

The following detailed description should be read with reference to the drawings in which similar elements in different drawings are numbered the same. The detailed description and the drawings, which are not necessarily to scale, depict illustrative embodiments and are not intended to limit the scope of the invention. The illustrative embodiments depicted are intended only as exemplary. Selected features of any illustrative embodiment may be incorporated into an additional embodiment unless clearly stated to the contrary.

Referring now to FIG. 1, there is shown a first exemplary embodiment of a vertebral anchor 10, shown as a polyaxial pedicle screw. The vertebral anchor 10 may include several components. For example, the vertebral anchor 10 may include a housing 12 pivotally coupled to a bone screw 14. The bone screw 14 may include a shaft portion 16, which may in some instances be threaded, extending from a head portion 18, which may in some instances be spherically shaped. The shaft 16 may be configured to be installed into a bony region of a vertebra of the spinal column. For example, the shaft 16 may be installed into a pedicle of a vertebra, or other region of a vertebra. The bone screw 4 may be pivotable relative to the housing 12 such that the longitudinal axis of the bone screw 14 is positioned at one of multiple angular orientations relative to the longitudinal axis of the housing 12.

The housing 12 may include a channel 20, such as a U-shaped channel extending from one side of the housing 12 to an opposite second side of the housing 12. The channel 20 may be defined between opposing first and second legs 22, 24 of the housing 12. The housing 12 may also include a bore 26 extending through the housing 12 along a longitudinal axis from the upper end 28 to the lower end 30 of the housing 12 which intersects the channel 20.

The housing 12 of the vertebral anchor 10 may be configured to receive an elongate member 40 of a vertebral stabilization system, such as a rigid or flexible fixation element, including a spinal rod or flexible cord, therein. For example, the channel 20 may be open to the upper end 28 of the housing 12 such that the elongate member 40 may be positioned in the channel 20 in a top-loaded fashion in which the elongate member 40 is moved into the channel 20 of the housing 12 in a direction generally perpendicular to the longitudinal axis of the channel 20 of the housing 12.

The vertebral anchor 10 may also include a securing element, such as a threaded fastener 34 (e.g., a set screw, cap) configured to rotatably engage the housing 12 to secure a portion of the elongate member 40 in the channel 20. For example, the threaded fastener 34 may include threads which mate with a threaded portion 32 formed in the legs 22, 24 of the housing 12. In other embodiments, the fastener 34 may include one or more flanges, cam surfaces, or other engagement features that engage with one or more channels, grooves, surfaces, or other engagement features of the housing 12 through rotation of the fastener 34. The fastener 34 may be rotatably engaged between the spaced apart legs 22, 24 of the housing 12 which define the channel 20 therebetween.

The vertebral anchor 10 may also include one or more components for coupling the housing 12 to the head portion 18 of the bone screw 14. For instance, the vertebral anchor 10 may include a retainer 42 positionable in the bore 26 of the housing 12 which includes a cavity 44 for receiving the head portion 18 of the bone screw 14 therein. In some instances, the cavity 44 may be a spherically concave cavity complementing the spherical shape of the head portion 18 of the bone screw 14. The retainer 42 may be formed of a resilient material, such as a pliable polymeric material or a malleable metallic material, providing the retainer 42 a desired amount of flexibility. The retainer 42 may also include a plurality of alternating tabs 46 and slots 48 spaced around a periphery of the retainer 42 enhancing the flexibility of the retainer 42. For example, a radially inward force may be exerted on the tabs 46 to deflect the tabs 46 radially inward to radially compress the retainer 42, whereas a radially outward force may be exerted on the tabs 46 to deflect or splay the tabs 46 radially outward to radially enlarge the lower opening into the cavity 44 of the retainer 42.

The retainer 42 illustrated in FIG. 1 includes a first subset of slots 48a opening out to the upper end of the retainer 42 and a second subset of slots 48b opening out to the lower end of the retainer 42. The slots 48a may alternate with the slots 48b around the circumference of the retainer 42.

The vertebral anchor 10 may also include a spacer 50 extending from the retainer 42 toward the upper end 28 of the housing 12. The spacer 50 may be axially movable relative to the retainer 42. The spacer 50 may include a first portion extending from the retainer 42 which is configured to engage an elongate stabilization member 40 disposed in the channel 20 of the housing 12 and a second portion extending into a bore of the retainer 42 which is configured to engage the head portion 8 of the bone screw 14. The spacer 50 may include an enlarged annular portion positioned in the bore of the retainer 42 which interlocks with a radially inward extending annular lip of the retainer 42.

The vertebral anchor 10 may further include a resilient spring means biasing the retainer 42 toward the lower end 30 of the housing 12. As shown in FIG. 1, the resilient spring means may be a wave washer 52, however, in other instances the resilient spring means may be a helical spring, elastomeric member, an integral portion of the retainer 42, or another structure configured to urge the retainer 42 toward the lower end 30 of the housing 12.

Figure 1A:
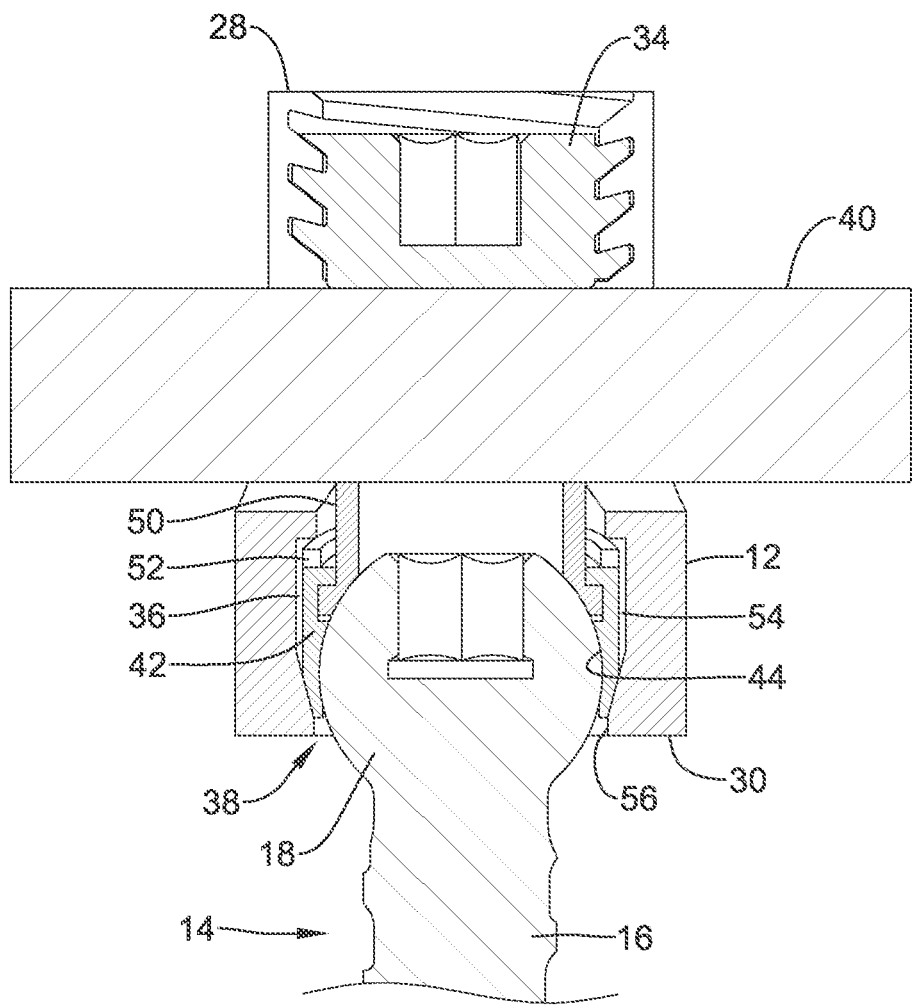
FIG. 1A is a cross-sectional view of the vertebral anchor of FIG. 1 with the housing coupled to the head portion of the bone screw.

The arrangement of components for coupling the housing 12 to the head portion 18 of the bone screw 14 is further illustrated in FIG. 1A. As shown in FIG. 1A, the retainer 42 may be positioned in an enlarged portion 36 of the bore 26, surrounding the head portion 18 of the bone screw 14. The spacer 50 may be positioned between the retainer 42 and the elongate member 40, a portion of the spacer 50 extending into the bore of the retainer 42 and directly engaging the head portion 18 of the bone screw 14. The wave washer 52 may be positioned in the bore 26 of the housing 12 and compressed between an annular rim of the housing 12 facing the lower end 30 of the housing 12 and an annular surface of the retainer 42 and/or spacer 50 facing the upper end 28 of the housing 12.

The retainer 42 may be movable in the bore 26 of the housing 12 along the longitudinal axis of the bore 26 between a first position in which the retainer 42 is closer to the lower end 30 of the housing 12 and a second position in which the retainer 42 is closer to the upper end 28 of the housing 12. The wave washer 52, or other resilient biasing means, may bias the retainer 42 toward the first position until a sufficient force is applied to the retainer 42 to overcome the biasing force of the wave washer 52 and moves the retainer 42 to the second position.

The retainer 42 may have an outermost diameter which is greater than the diameter of the lower opening 38 of the bore 26 extending through the housing 12, yet the outermost diameter of the retainer 42 may be less than an enlarged portion 36 of the bore 26 in which the retainer 42 is positioned, providing an annular space 54 between the outer circumferential surface of the retainer 42 and the circumferential surface of the bore 26. In some instances, the housing 12 may include an annular rim 56 defining the lower opening 38, in which the diameter of the lower opening 38 at the annular rim 56 is less than a diameter of the enlarged portion 36 of the bore 26 of the housing 12 toward the upper end 28 of the housing 12 from the annular rim 56. When in the first position, the wave washer 52 may push the retainer 42 against the annular rim 56, preventing the retainer 42 from radially expanding.

During assembly of the vertebral anchor 10, the retainer 42, as well as the wave washer 52 and the spacer 50 may be inserted into the lower opening 38 of the housing 12. For example, the plurality of alternating tabs 46 and slots 48 formed around the circumference of the retainer 42 may provide the retainer 42 with sufficient flexibility to be urged through the lower opening 38 from the tower end 30 of the housing 12 by radially compressing the retainer 42.

Figure 1B:
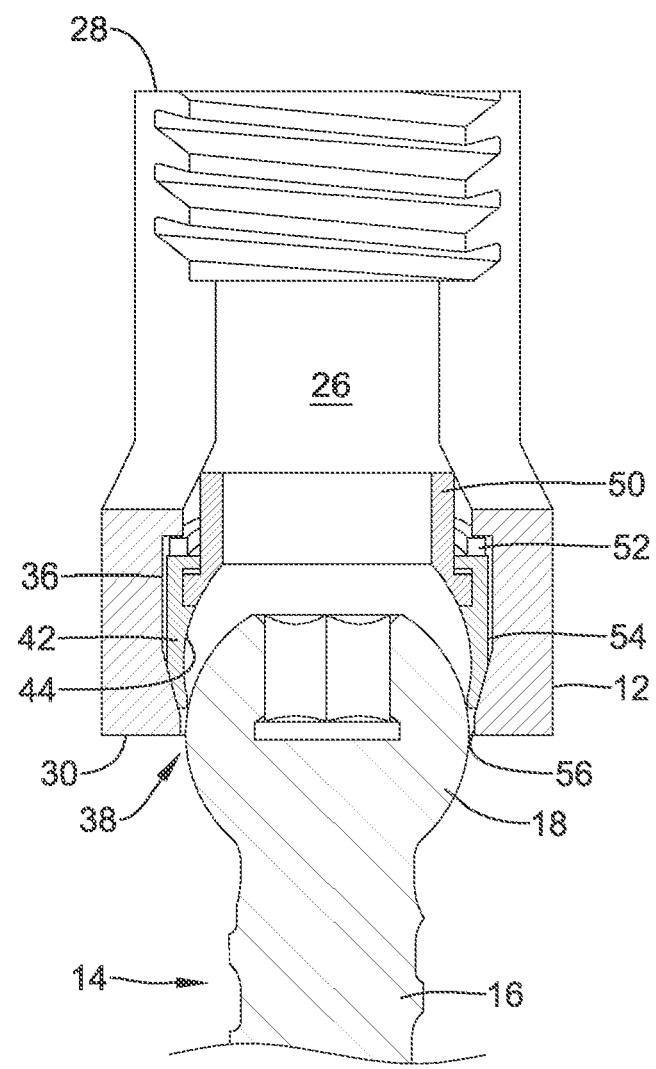
FIG. 1B is a cross-sectional view of the vertebral anchor of FIG. 1 while coupling the housing to the head portion of the bone screw.

With the retainer 42, resilient spring means (e.g., the wave washer 52) and other components positioned in the bore 26 of the housing 12, the head portion 18 of the bone screw 14 may be inserted into the cavity 44 of the retainer 42 through the lower opening 38 from the lower end 30 in a bottom loaded manner. The diameter of the head portion 18 of the bone screw 14 may be less than the diameter of the lower opening 38 at the annular rim 56 to allow the head portion 18 to pass therethrough. As shown in FIG. 1B, the head portion 18 of the bone screw 14, or another structure, may apply a force against the retainer 42 opposing and overcoming the biasing force of the wave washer 52 which urges the retainer 42 to the second position in which the retainer 42 is moved toward the upper end 28 of the housing 12 along the longitudinal axis of the bore 26. Now positioned in an enlarged diameter portion 36 of the bore 26 and radially unconstrained by the interior surface of the bore 26 and/or the annular rim 56 at the lower opening 38 of the housing 12, the flexibility of the retainer 42 allows the retainer 42 to radially expanded. For example, the plurality of tabs 46 of the retainer 42 may be deflected radially outward in order to allow the head portion 18 of the bone screw 14 to pass into the cavity 44 of the retainer 42. The presence of the annular space 54 allows the retainer 42 to radially expand to accommodate insertion of the head portion 18 into the cavity 44.

Once the head portion 18 of the bone screw 14 is positioned in the cavity 44, the applied force to the retainer 42 may be removed, allowing the biasing force of the wave washer 52 or other biasing means to move the retainer 42 back to the first position toward the lower end 30 of the housing 12 and into engagement with the reduced diameter annular portion of the housing 12 to prevent further radial expansion or splaying of the retainer 42. In some instances, the retainer 42 may include a lower beveled surface which contacts the annular rim 56 of the housing 12 to urge the tabs 46 of the retainer 42 radially inward and/or prevent radial splaying to secure the head portion 18 of the hone screw 14 in the cavity 44 of the retainer 42.

When an elongate member 40 is secured in the channel 20 of the housing 12, a clamping force may be exerted against the head portion 18 of the bone screw 14. However, because the lower opening of the retainer 42 when at the first position has a diameter less than the diameter of the head portion 18 of the bone screw 14, the head portion 18 is prevented from being removed from the cavity 44 of the retainer 42 since the annular rim 56 of the housing 12 resists expansion of the lower opening of the retainer 42 when pressed there against.

Figure 2:
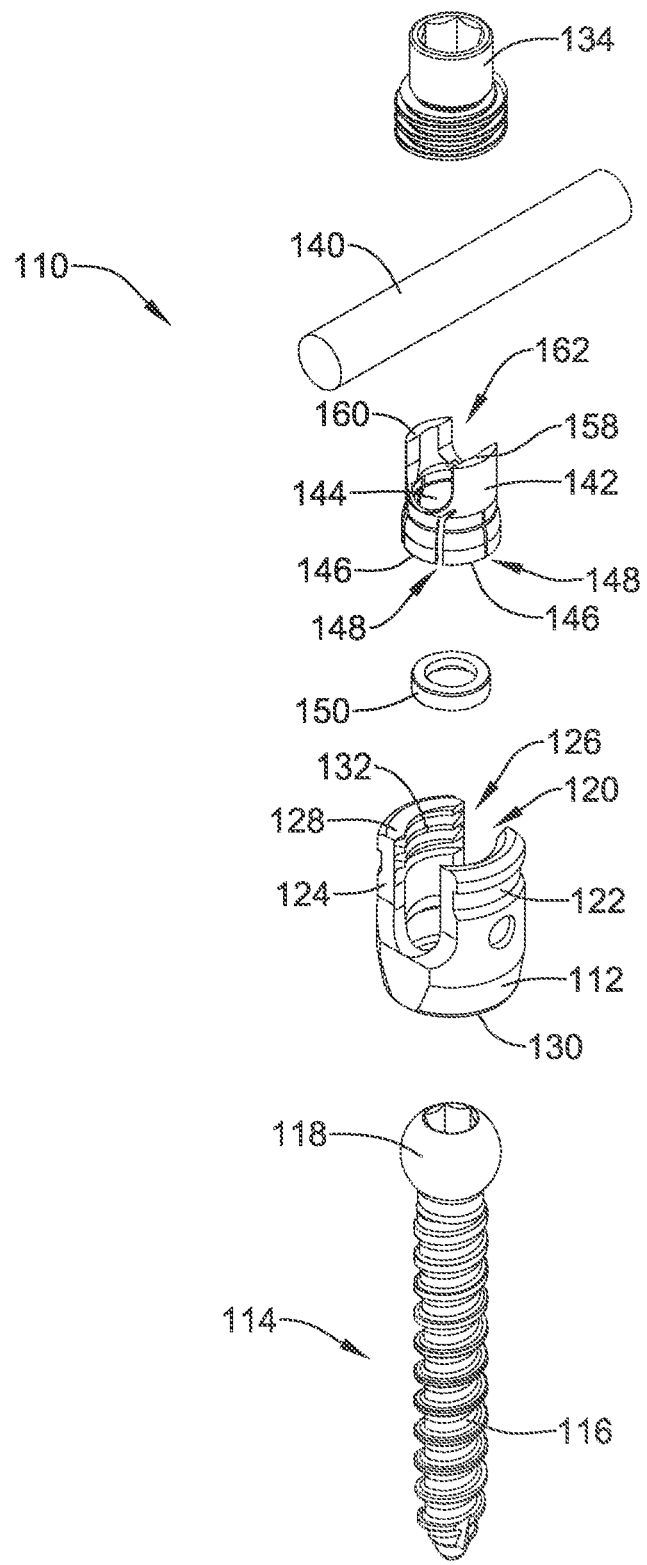
FIG. 2 is an exploded perspective view of components of another exemplary vertebral anchor.

Another exemplary embodiment of a vertebral anchor 110, shown as a polyaxial pedicle screw, is illustrated in FIG. 2. The vertebral anchor 110 may include several components. For example, the vertebral anchor 110 may include a housing 112 pivotably coupled to a bone screw 114. The bone screw 114 may include a shaft portion 116, which may in some instances be threaded, extending from a head portion 118, which may in some instances spherically shaped. The shaft 116 may be configured to be installed into a bony region of a vertebra of the spinal column. For example the shaft 116 may be installed into a pedicle of a vertebra, or other region of a vertebra. The bone screw 114 may be pivotable relative to the housing 112 such that the longitudinal axis of the bone screw 114 is positioned at one of multiple angular orientations relative to the longitudinal axis of the housing 112.

The housing 112 may include a channel 120, such as a U-shaped channel extending from one side of the housing 112 to an opposite second side of the housing 112. The channel 120 may be defined between opposing first and second legs 122, 124 of the housing 112. The housing 112 may also include a bore 126 extending through the housing 112 along a longitudinal axis from the upper end 128 to the lower end 130 of the housing 112 which intersects the channel 120.

The housing 112 of the vertebral anchor 10 may be configured to receive an elongate member 140 of a vertebral stabilization system, such as a rigid or flexible fixation element, including a spinal rod or flexible cord, therein. For example, the channel 120 may be open to the upper end 128 of the housing 112 such that the elongate member 140 may be positioned in the channel 120 in a top-loaded fashion in which the elongate member 140 is moved into the channel 120 of the housing 112 in a direction generally perpendicular to the longitudinal axis of the channel 120 of the housing 112.

The vertebral anchor 110 may also include a securing element, such as a threaded fastener 134 (e.g., a set screw, cap) configured to rotatably engage the housing 112 to secure a portion of the elongate member 140 in the channel 120. For example, the threaded fastener 134 may include threads which mate with a threaded portion 132 formed in the legs 122, 124 of the housing 112. In other embodiments, the fastener 134 may include one or more flanges, cam surfaces, or other engagement features that engage with one or more channels, grooves, surfaces, or other engagement features of the housing 112 through rotation of the fastener 134. The fastener 134 may be rotatably engaged between the spaced apart legs 122, 124 of the housing 112 which define the channel 120 therebetween.

The vertebral anchor 110 may also include one or more components coupling the housing 112 to the head portion 118 of the bone screw 114. For instance, the vertebral anchor 110 may include a retainer 142 positionable in the bore 126 of the housing 112 which includes a cavity 144 for receiving the head portion 118 of the bone screw 114 therein. In some instances, the cavity 144 may be a spherically concave cavity complementing the spherical shape of the head portion 118 of the bone screw 114. The retainer 142 may be formed of a resilient material, such as a pliable polymeric material or a malleable metallic material, providing the retainer 142 a desired amount of flexibility. A lower portion of the retainer 142 may also include a plurality of alternating tabs 146 and slots 148 spaced around a periphery of the lower portion of the retainer 142 enhancing the flexibility of the lower portion of the retainer 142. For example, a radially inward force may be exerted on the tabs 146 to deflect the tabs 146 radially inward to radially compress the retainer 142, whereas a radially outward force may be exerted on the tabs 146 to deflect or splay the tabs 146 radially outward to radially enlarge the lower opening into the cavity 144 of the retainer 142.

The upper portion of the retainer 142 illustrated in FIG. 2 may further include first and second legs 158, 160 defining a channel 162 therebetween aligned with the channel 120 of the housing 112 for receiving an elongate stabilization member 140 therethrough.

The vertebral anchor 110 may also include a spacer 150 extending from the retainer 142 toward the upper end 128 of the housing 112. The spacer 150 may be axially movable relative to the retainer 142. The spacer 150 may include a first portion extending from the retainer 142 which is configured to engage an elongate stabilization member 140 disposed in the channel 120 of the housing 112 and a second portion extending into a bore of the retainer 142 which is configured to engage the head portion 118 of the bone screw 114. In some instances, the spacer 150 may include structure, such as an enlarged annular portion which interlocks with structure of the retainer 142, such as an annular lip of the retainer 142.

In some instances, the vertebral anchor 110 may further include a resilient spring means (not shown) biasing the retainer 142 toward the lower end 130 of the housing 112. In some instances, the resilient spring means may be a wave washer, a helical spring, elastomeric member, an integral portion of the retainer 142, or another structure configured to urge the retainer 142 toward the lower end 130 of the housing 112.

Figure 2A:
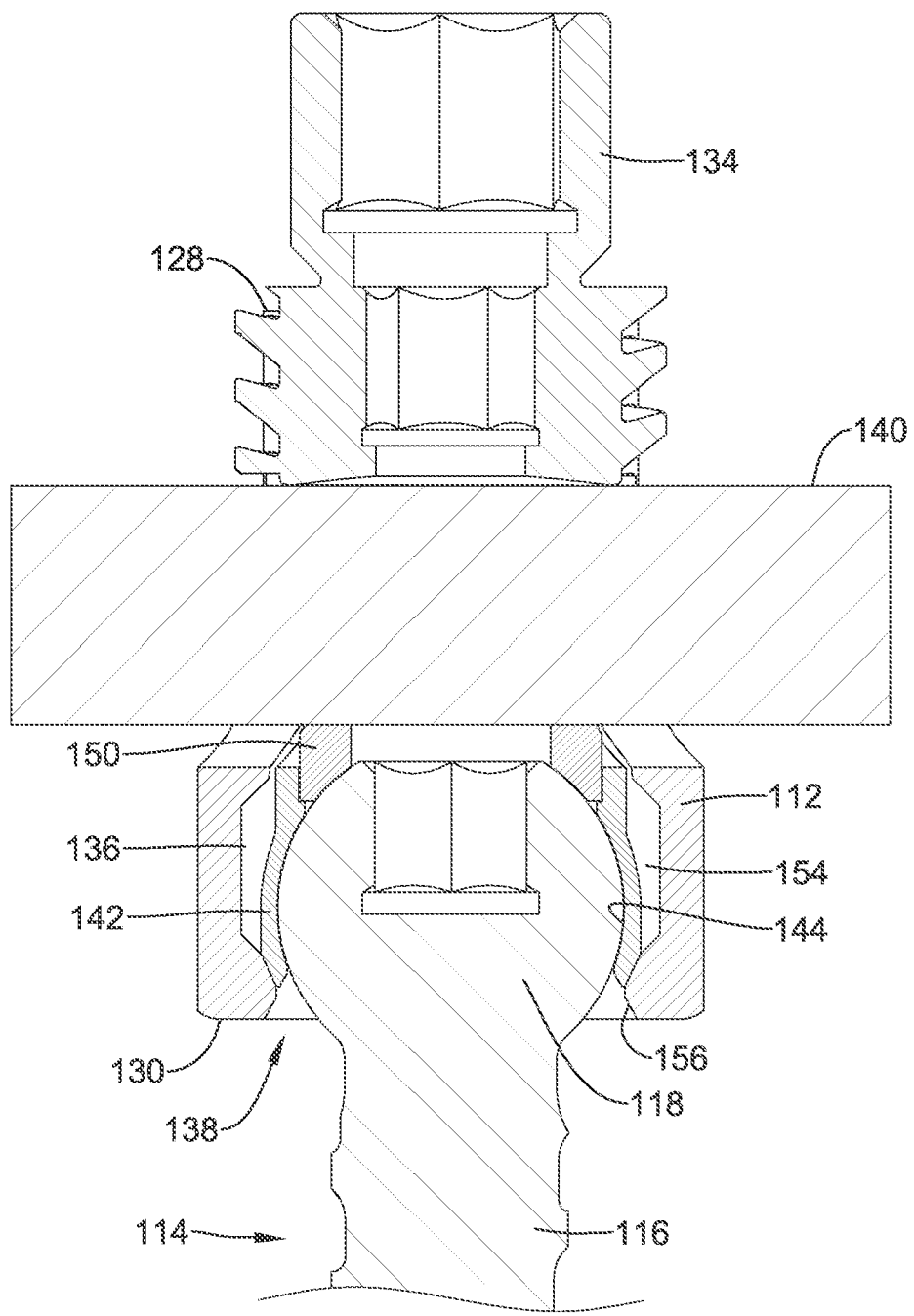
FIG. 2A is a cross-sectional view of the vertebral anchor of FIG. 2 with the housing coupled to the head portion of the bone screw.
Figure 2B:
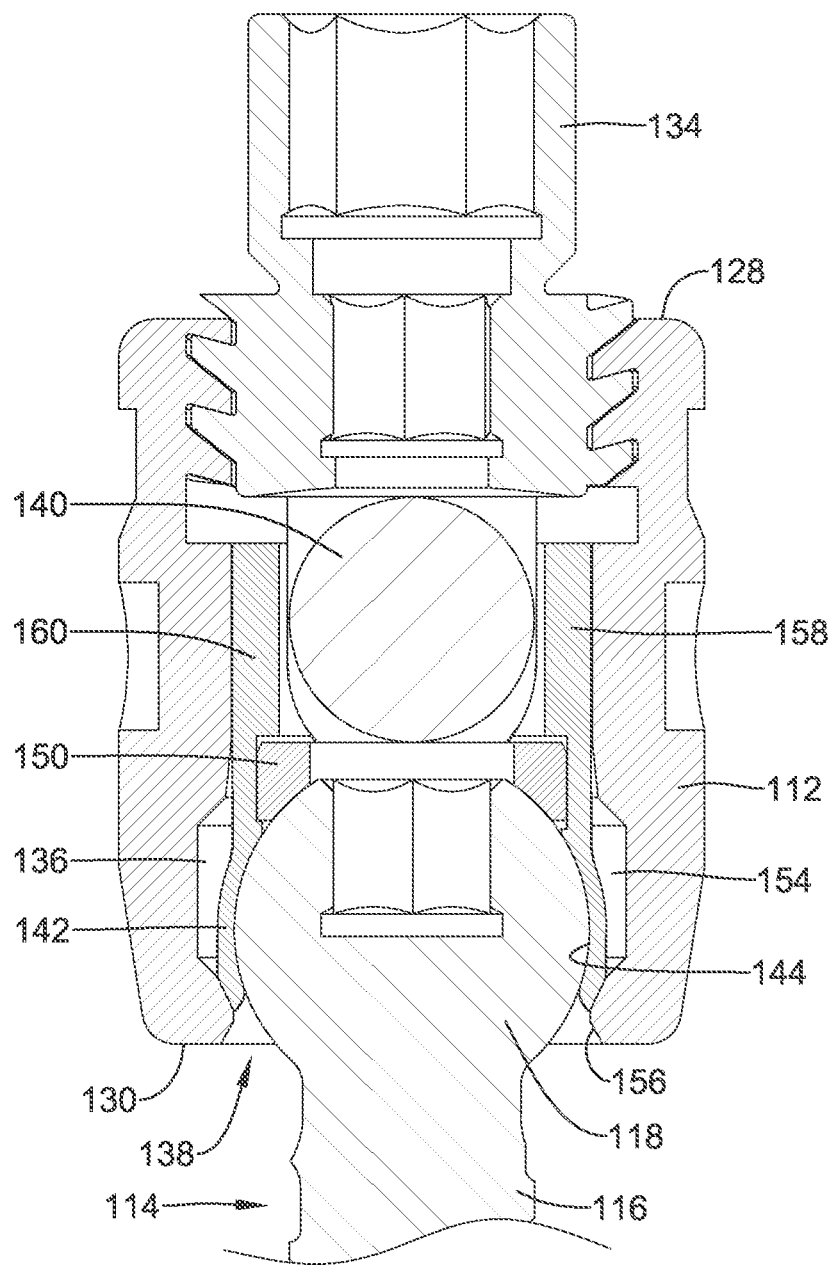
FIG. 2B is a cross-sectional view of the vertebral anchor of FIG. 2, transverse to the cross-sectional view of FIG. 2A, with the housing coupled to the head portion of the bone screw.

The arrangement of components for coupling the housing 112 to the head portion 118 of the bone screw 114 is further illustrated in FIGS. 2A and 2B. As shown, the lower portion of the retainer 142 may be positioned in an enlarged portion 136 of the bore 126, surrounding the head portion 118 of the bone screw 114. The legs 158, 160 of the retainer 142 may be aligned with the legs 122, 124 of the housing 112 such that the channel 162 defined between the legs 158, 160 is aligned with the channel 120 defined between the legs 122, 124 of the housing 112. The spacer 150 may be positioned between the retainer 142 and the elongate member 140, with a portion of the spacer 150 extending into the bore of the retainer 142 and directly engaging the head portion 118 of the bone screw 114.

The retainer 142 may be movable in the bore 126 of the housing 112 along the longitudinal axis of the bore 126 between a first position in which the retainer 142 is closer to the lower end 130 of the housing 112 and a second position in which the retainer 142 is closer to the upper end 128 of the housing 112. In some instances, a resilient biasing means, such as a wave washer, a helical spring, elastomeric member, an integral portion of the retainer 142, or another structure, may bias the retainer 142 toward the first position until a sufficient force is applied to the retainer 142 to overcome the biasing force of the wave washer 152 and moves the retainer 142 to the second position.

The retainer 142 may have an outermost diameter which is greater than the diameter of the lower opening 138 of the bore 126 extending through the housing 112, yet the outmost diameter of the retainer 142 may be less than an enlarged portion 136 of the bore 126 in which the retainer 142 is positioned, providing an annular space 154 between the outer circumferential surface of the retainer 142 and the circumferential surface of the bore 126. In some instances, the housing 112 may include an annular rim 156 defining the lower opening 138, in which the diameter of the lower opening 138 at the annular rim 156 is less than a diameter of the portion 136 of the bore 126 of the housing 112 toward the upper end 128 of the housing 112 from the annular rim 156. When in the first position, a resilient biasing member may push the retainer 142 against the annular rim 156, preventing the retainer 142 from radially expanding. Alternatively, a clamping force exerted against the elongate member 140 by the fastener 134 may exert a force through the spacer 150 to the retainer 142, push the retainer 142 against the annular rim 156.

During assembly of the vertebral anchor 110, the retainer 142 and the spacer 150 may be inserted into the bore 126 of the housing 112 through the lower opening 138 of the housing 112 or from the upper end 128 of the housing 112. For example, the plurality of alternating tabs 146 and slots 148 formed around the circumference of the retainer 142 may provide the retainer 142 with sufficient flexibility to be radially compressed when being inserted into the bore 126.

Figure 2C:
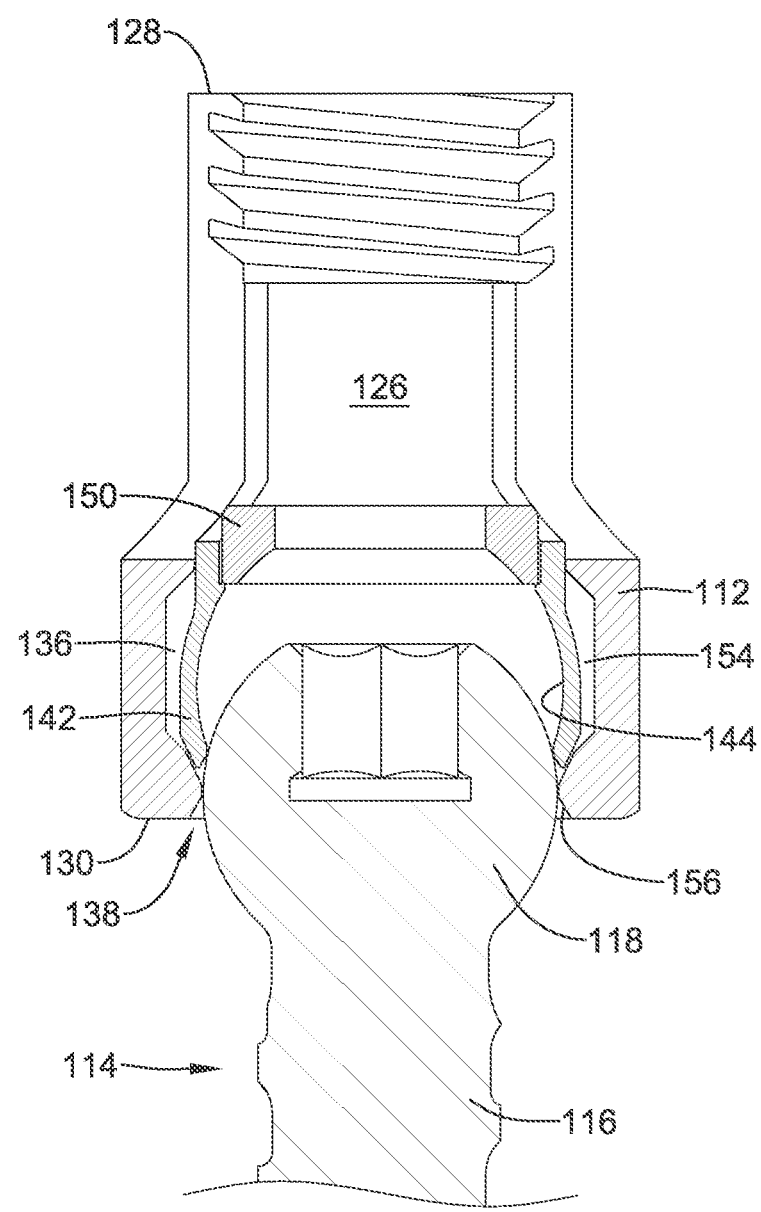
FIG. 2C is a cross-sectional view of the vertebral anchor of FIG. 2 while coupling the housing to the head portion of the bone screw.

With the retainer 142, spacer 150, and resilient spring means if present, positioned in the bore 126 of the housing 112, the head portion 118 of the bone screw 114 may be inserted into the cavity 144 of the retainer 142 through the lower opening 138 from the lower end 130 in a bottom loaded manner. The diameter of the head portion 118 of the bone screw 114 may be less than the diameter of the lower opening 138 at the annular rim 156 to allow the head portion 118 to pass therethrough. As shown in FIG. 2C, the head portion 118 of the bone screw 114, or another structure, may apply a force against the retainer 142 opposing and overcoming any biasing force, and thus urging the retainer 142 to the second position in which the retainer 142 is moved toward the upper end 128 of the housing 112 along the longitudinal axis of the bore 126. Now positioned in an enlarged diameter portion 136 of the bore 126 and radially unconstrained by interior surface of the bore 126 and/or the annular rim 156 at the lower opening 138 of the housing 112, the flexibility of the retainer 142 allows the lower portion of the retainer 142 to be radially expanded. For example, the plurality of tabs 146 of the retainer 142 may be deflected radially outward in order to allow the head portion 118 of the bone screw 114 to pass into the cavity 144 of the retainer 142. The presence of the annular space 154 allows the retainer 142 to radially expand to accommodate insertion of the head portion 118 into the cavity 144.

Once the head portion 118 of the bone screw 114 is positioned in the cavity 144, the applied force to the retainer 142 may be removed, allowing the retainer 142 to move back to the first position toward the lower end 130 of the housing 112 and into engagement with the reduced diameter annular portion of the housing 112 to prevent further radial expansion or splaying of the lower portion of the retainer 142. In some instances, the retainer 142 may include a lower beveled surface which contacts the annular rim 156 of the housing 112 to urge the tabs 146 of the retainer 142 radially inward and/or prevent radial splaying to secure the head portion 118 of the hone screw 114 in the cavity 144 of the retainer 142.

When an elongate member 140 is secured in the channel 120 of the housing 112, a clamping force may be exerted against the head portion 118 of the bone screw 114. However, because the lower opening of the retainer 142 when at the first position as a diameter less than the diameter of the head portion 118 of the bone screw 114 the head portion 118 is prevented from being removed from the cavity 144 of the retainer 142 since the annular rim 156 of the housing 112 resists radial expansion of the lower opening of the retainer 142 when pressed thereagainst.

Figure 3:
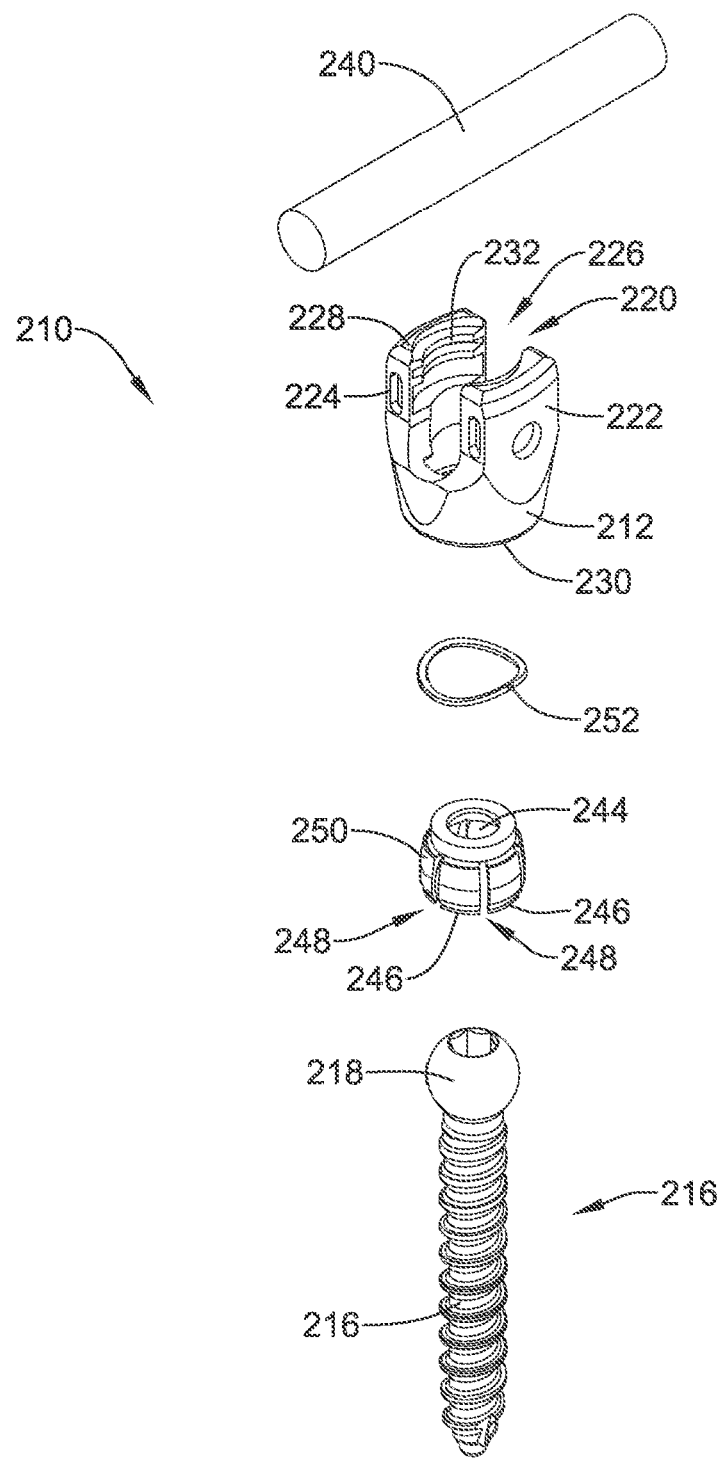
FIG. 3 is an exploded perspective view of components of another exemplary vertebral anchor.

Another exemplary embodiment of a vertebral anchor 210, shown as a polyaxial pedicle screw, is illustrated in FIG. 3. The vertebral anchor 210 may include several components. For example, the vertebral anchor 210 may include a housing 212 pivotably coupled to a bone screw 214. The bone screw 214 may include a shaft portion 216, which may in some instances be threaded, extending from a head portion 218, which may in some instances be spherically shaped. The shaft 216 may be configured to be installed into a bony region of a vertebra of the spinal column. For example, the shaft 216 may be installed into a pedicle of a vertebra, or other region of a vertebra. The bone screw 214 may be pivotable relative to the housing 212 such that the longitudinal axis of the bone screw 214 is positioned at one of multiple angular orientations relative to the longitudinal axis of the housing 212.

The housing 212 may include a channel 220, such as a U-shaped channel extending from one side of the housing 212 to an opposite second side of the housing 212. The channel 220 may be defined between opposing first and second legs 222, 224 of the housing 212. The housing 212 may also include a bore 226 extending through the housing 212 along a longitudinal axis from the upper end 228 to the lower end 230 of the housing 212 which intersects the channel 220.

The housing 212 of the vertebral anchor 210 may be configured to receive an elongate member 240 of a vertebral stabilization system, such as a rigid or flexible fixation element, including a spinal rod or flexible cord, therein. For example, the channel 220 may be open to the upper end 228 of the housing 212 such that the elongate member 240 may be positioned in the channel 220 in a top-loaded fashion in which the elongate member 240 is moved into the channel 220 of the housing 212 in a direction generally perpendicular to the longitudinal axis of the channel 220 of the housing 212.

The vertebral anchor 210 may also include a securing element, such as a threaded fastener (not shown) configured to rotatably engage the housing 212 to secure a portion of the elongate member 240 in the channel 220. For example, the threaded fastener may include threads which mate with a threaded portion 232 formed in the legs 222, 224 of the housing 212. In other embodiments, the fastener may include one or more flanges, cam surfaces, or other engagement features that engage with one or more channels, grooves, surfaces, or other engagement features of the housing 212 through rotation of the fastener. The fastener may be rotatably engaged between the spaced apart legs 222, 224 of the housing 212 which define the channel 220 therebetween.

The vertebral anchor 210 may also include one or more components for coupling the housing 212 to the head portion 218 of the bone screw 214. For instance, the vertebral anchor 210 may include a retainer 242 positionable in the bore 226 of the housing 212 which includes a cavity 244 for receiving the head portion 218 of the bone screw 214 therein. In some instances, the cavity 244 may be a spherically concave cavity complementing the spherical shape of the head portion 218 of the bone screw 214. The retainer 242 may be formed of a resilient material, such as a pliable polymeric material or a malleable metallic material, providing the retainer 242 a desired amount of flexibility. The retainer 242 may also include a plurality of alternating tabs 246 and slots 248 spaced around a periphery of the retainer 242 enhancing the flexibility of the retainer 242. For example, a radially inward force may be exerted on the tabs 246 to deflect the tabs 246 radially inward to radially compress the retainer 242, whereas a radially outward force may be exerted on the tabs 246 to deflect or splay the tabs 246 radially outward to radially enlarge the lower opening into the cavity 244 of the retainer 242.

The vertebral anchor 210 may further include a resilient spring means biasing the retainer 242 toward the lower end 230 of the housing 212. As shown in FIG. 3, the resilient spring means may be a wave washer 252, however, in other instances the resilient spring means may be a helical spring, elastomeric member, an integral portion of the retainer 242, or another structure configured to urge the retainer 242 toward the lower end 230 of the housing 212.

Figure 3A:
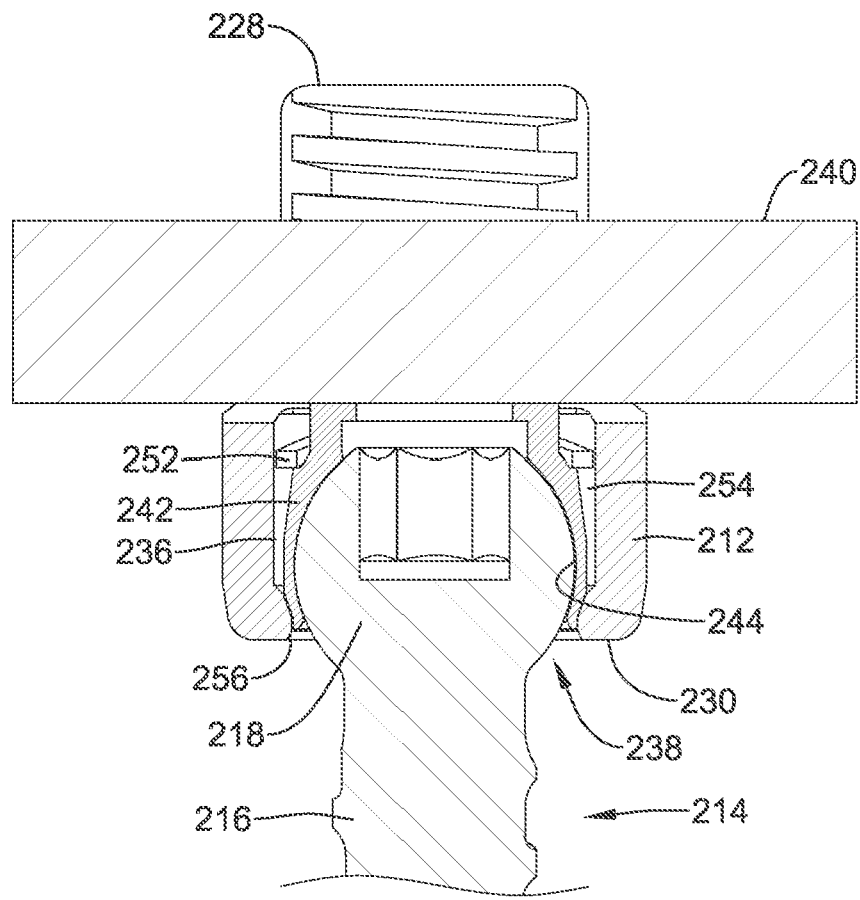
FIG. 3A is a cross-sectional view of the vertebral anchor of FIG. 3 with the housing coupled to the head portion of the bone screw.

The arrangement of components for coupling the housing 212 to the head portion 218 of the bone screw 214 is further illustrated in FIG. 3A. As shown in FIG. 3A, the retainer 242 may be positioned in an enlarged portion 236 of the bore 226, surrounding the head portion 218 of the bone screw 214. The wave washer 252 may be positioned in the bore 226 of the housing 212 and compressed between an annular rim of the housing 212 facing the lower end 230 of the housing 212 and an annular surface of the retainer 242 facing the upper end 228 of the housing 212. An upper portion of the retainer 242 may extend through the wave washer 252 to directly engage the elongate member 240.

The retainer 242 may be movable in the bore 226 of the housing 212 along the longitudinal axis of the bore 226 between a first position in which the retainer 242 is closer to the lower end 230 of the housing 212 and a second position in which the retainer 242 is closer to the upper end 228 of the housing 212. The wave washer 252, or other resilient biasing means, may bias the retainer 242 toward the first position until a sufficient force is applied to the retainer 242 to overcome the biasing force of the wave washer 252 and moves the retainer 242 to the second position.

The retainer 242 may have an outermost diameter which is greater than the diameter of the lower opening 238 of the bore 226 extending through the housing 212, yet the outermost diameter of the retainer 242 may be less than an enlarged portion 236 of the bore 226 in which the retainer 242 is positioned, providing an annular space 254 between the outer circumferential surface of the retainer 242 and the circumferential surface of the bore 226. In some instances, the housing 212 may include an annular rim 256 defining the lower opening 238, in which the diameter of the lower opening 238 at the annular rim 256 is less than a diameter of the enlarged portion 236 of the bore 226 of the housing 212 toward the upper end 228 of the housing 212 from the annular rim 256. When in the first position, the wave washer 252 may push the retainer 242 against the annular rim 256, preventing the retainer 242 from radially expanding.

During assembly of the vertebral anchor 210, the retainer 242, as well as the wave washer 252, may be inserted into the lower opening 238 of the housing 212. For example, the plurality of alternating tabs 246 and slots 248 formed around the circumference of the retainer 242 may provide the retainer 242 with sufficient flexibility to be urged through the lower opening 238 from the lower end 230 of the housing 212 by radially compressing the retainer 242.

Figure 3B:
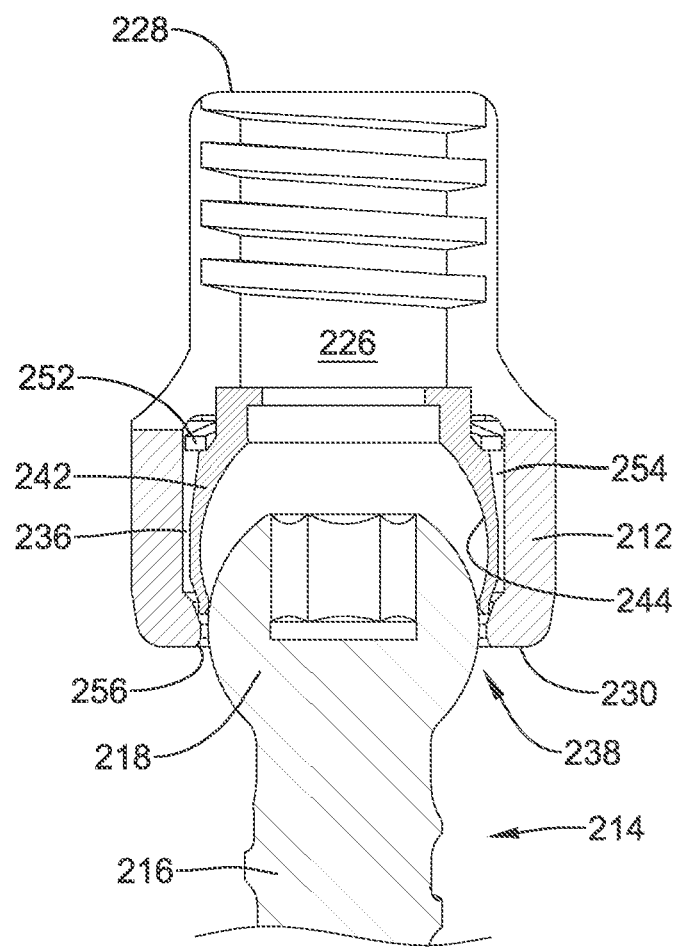
FIG. 3B is a cross-sectional view of the vertebral anchor of FIG. 3 while coupling the housing to the head portion of the bone screw.

With the retainer 242, resilient spring means (e.g., the wave washer 252) and any components positioned in the bore 226 of the housing 212, the head portion 218 of the bone screw 214 may be inserted into the cavity 244 of the retainer 242 through the lower opening 238 from the lower end 230 in a bottom loaded manner. The diameter of the head portion 218 of the bone screw 214 may be less than the diameter of the lower opening 238 at the annular rim 256 to allow the head portion 218 to pass therethrough. As shown in FIG. 3B, the head portion 218 of the bone screw 214, or another structure, may apply a force against the retainer 242 opposing and overcoming the biasing force of the wave washer 252 which urges the retainer 242 to the second position in which the retainer 242 is moved toward the upper end 228 of the housing 212 along the longitudinal axis of the bore 226. Now positioned in an enlarged diameter portion 236 of the bore 226 and radially unconstrained by the interior surface of the bore 226 and/or the annular rim 256 at the lower opening 238 of the housing 212, the flexibility of the retainer 242 allows the retainer 242 to be radially expanded. For example, the plurality of tabs 246 of the retainer 242 may be deflected radially outward in order to allow the head portion 218 of the bone screw 214 to pass into the cavity 244 of the retainer 242. The presence of the annular space 254 allows the retainer 242 to radially expand to accommodate insertion of the head portion 218 into the cavity 244.

Once the head portion 218 of the bone screw 214 is positioned in the cavity 244, the applied force to the retainer 242 may be removed, allowing the biasing force of the wave washer 252 or other biasing means to move the retainer 242 back to the first position toward the lower end 230 of the housing 212 and into engagement with the reduced diameter annular portion of the housing 212 to prevent further radial expansion or splaying of the retainer 242. In some instances, the retainer 242 may include a lower beveled surface which contacts the annular rim 256 of the housing 212 to urge the tabs 246 of die retainer 242 radially inward and/or prevent radial splaying to secure the head portion 218 of the bone screw 214 in the cavity 244 of the retainer 242.

When an elongate member 240 is secured in the channel 220 of the housing 212, a clamping force may be exerted against the head portion 218 of the bone screw 214. However, because the lower opening of the retainer 242 when at the first position has a diameter less than the diameter of the head portion 218 of the bone screw 214, the head portion 218 is prevented from being removed from the cavity 244 of the retainer 242 since the annular rim 256 of the housing 212 resists radial expansion of the lower opening of the retainer 242 when pressed thereagainst.

Figure 4:
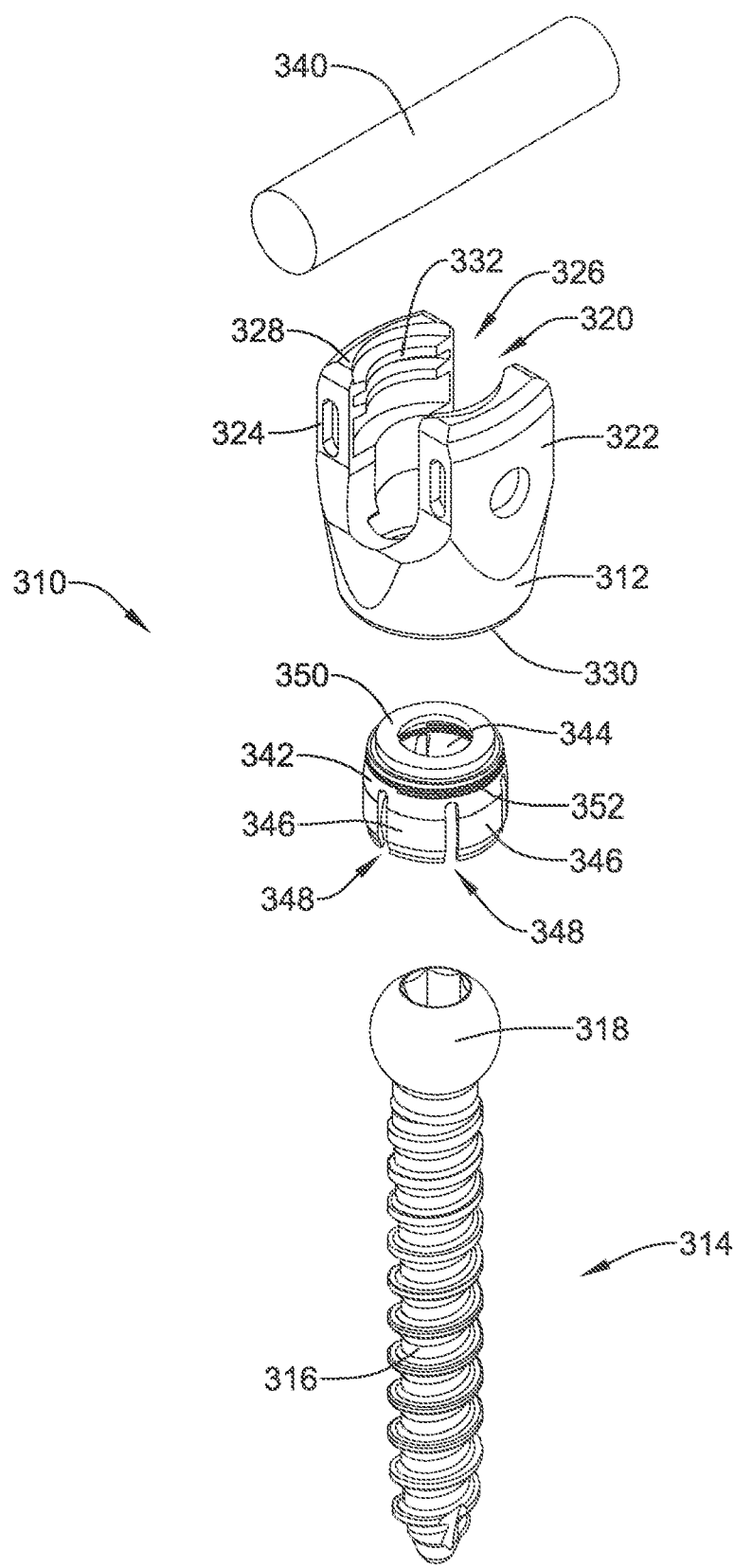
FIG. 4 is an exploded perspective view of components of another exemplary vertebral anchor.

Another exemplary embodiment of a vertebral anchor 310, shown as a polyaxial pedicle screw, is illustrated in FIG. 4. The vertebral anchor 310 may include several components. For example, the vertebral anchor 310 may include a housing 312 pivotably coupled to a bone screw 314. The bone screw 314 may include a shaft portion 316, which may in some instances be threaded, extending from a head portion 318, which may in some instances be spherically shaped. The shaft 316 may be configured to be installed into a bony region of a vertebra of the spinal column. For example, the shaft 316 may be installed into a pedicle of a vertebra, or other region of a vertebra. The bone screw 314 may be pivotable relative to the housing 312 such that the longitudinal axis of the bone screw 314 is positioned at one of multiple angular orientations relative to the longitudinal axis of the housing 312.

The housing 312 include a channel 320, such as a U-shaped channel extending from one side of the housing 312 to an opposite second side of the housing 312. The channel 320 may be defined between opposing first and second legs 322, 324 of the housing 312. The housing 312 may also include a bore 326 extending through the housing 312 along a longitudinal axis from the upper end 328 to the lower end 330 of the housing 312 which intersects the channel 390.

The housing 312 of the vertebral anchor 310 may be configured to receive an elongate member 340 of a vertebral stabilization system, such as a rigid or flexible fixation element, including a spinal rod or flexible cord, therein. For example, the channel 320 may be open to the upper end 328 of the housing 312 such that the elongate member 340 may be positioned in the channel 320 in a top-loaded fashion in which the elongate member 340 is moved into the channel 320 of the housing 312 in a direction generally perpendicular to lie longitudinal axis of the channel 320 of the housing 312.

The vertebral anchor 310 may also include a securing element, such as a threaded fastener (not shown) configured to rotatably engage the housing 312 to secure a portion of the elongate member 340 in the channel 320. For example, the threaded fastener may include threads which mate with a threaded portion 332 formed in the legs 322, 324 of the housing 312. In other embodiments, the fastener may include one or more flanges, cam surfaces, or other engagement features that engage with one or more channels, grooves, surfaces, or other engagement features of the housing 312 through rotation of the fastener. The fastener may be rotatably engaged between the spaced apart legs 322, 324 of the housing 312 which define the channel 320 therebetween.

The vertebral anchor 310 may also include one or more components for coupling the housing 312 to the head portion 318 of the bone screw 314. For instance, the vertebral anchor 310 may include a retainer 342 positionable in the bore 326 of the housing 312 which includes a cavity 344 for receiving the head portion 318 of the bone screw 314 therein. In some instances, the cavity 344 may be a spherically concave cavity complementing the spherical shape of the head portion 318 of the bone screw 314. The retainer 342 may be formed of a resilient material, such as a pliable polymeric material or a malleable metallic material, providing the retainer 342 a desired amount of flexibility. The retainer 342 may also include a plurality of alternating tabs 346 and slots 348 spaced around a periphery of the retainer 342 enhancing the flexibility of the retainer 342. For example, a radially inward force may be exerted on the tabs 346 to deflect the tabs 346 radially inward to radially compress the retainer 342, whereas a radially outward force may be exerted on the tabs 346 to deflect or splay the tabs 346 radially outward to radially enlarge the lower opening into the cavity 344 of the retainer 342.

The vertebral anchor 310 may further include a resilient spring means biasing the retainer 342 toward the lower end 330 of the housing 312. As shown in FIG. 4, the resilient spring means may an integral portion of the retainer 342. For instance, the retainer 342 may be a portion of the retainer 342 including one or more circumferential or helical slots 352 formed therein. Circumferential slots may extend less than 360° around the circumference, whereas a helical slot may extend less than, greater than or equal to 360° around the retainer 342. The slots 352 may be interposed between an annular upper portion 350 and the lower portion including the tabs 346 and defining the cavity 344. Thus, the retainer 342 may be a monolithic structure including the annular upper portion 350, the intermediate portion including the slots 352 and the lower portion including the tabs 346. However, in other embodiments, the resilient spring means may be a wave washer, a helical spring, elastomeric member, or another structure configured to urge the retainer 342 toward the lower end 330 of the housing 312.

The circumferential or helical slots 352 formed in the retainer 342 may allow the intermediate portion of the retainer 342 to be resiliently compressed between the annular upper portion 350 and the lower portion of the retainer 342. For example, when an axially compressive force is applied to the retainer 342, the axial length of the retainer 342 may be reduced as the width of the slots 352 is reduced. When the applied compressive force is removed or reduced, the axial length of the retainer 342 may be increased. Thus, the slots 352 formed around the intermediate portion may provide a pseudo-spring.

Figure 4A:
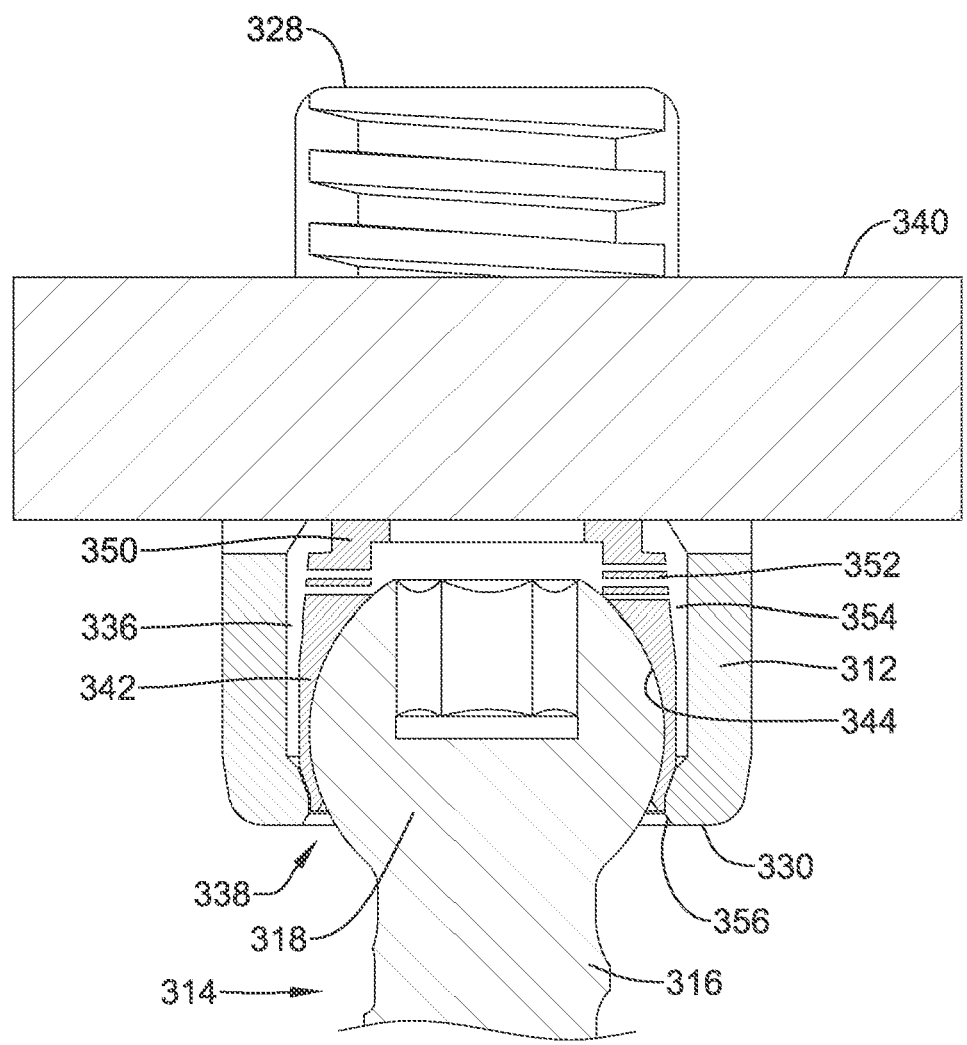
FIG. 4A is a cross-sectional view of the vertebral anchor of FIG. 4 with the housing coupled to the head portion of the bone screw.

The arrangement of components for coupling the housing 312 to the head portion 318 of the bone screw 314 is further illustrated in FIG. 4A. As shown in FIG. 4A, the retainer 342 may be positioned in an enlarged portion 336 of the bore 326, surrounding the head portion 318 of the bone screw 314. The upper portion 350 of the retainer 342 may directly engage the elongate member 340.

The retainer 342 may be movable in the bore 326 of the housing 312 along the longitudinal axis of the bore 326 between a first position in which the retainer 342 is closer to the lower end 330 of the housing 312 and a second position in which the retainer 342 is closer to the upper end 328 of the housing 312. The resilient nature of the compressed intermediate portion having the slots 352, or other resilient biasing means, may bias the retainer 342 toward the first position until a sufficient force is applied to the retainer 342 to overcome the biasing force of the intermediate portion having the slots 352 and moves the retainer 342 to the second position.

The retainer 342 may have an outermost diameter which is greater than the diameter of the lower opening 338 of the bore 326 extending through the housing 312, yet the outermost diameter of the retainer 342 may be less than an enlarged portion 336 of the bore 326 in which the retainer 342 is positioned, providing an annular space 354 between the outer circumferential surface of the retainer 342 and the circumferential surface of the bore 326. In some instances, the housing 312 may include an annular rim 356 defining the lower opening 338, in which the diameter of the lower opening 338 at the annular rim 356 is less than a diameter of the enlarged portion 336 of the bore 326 of the housing 312 toward the upper end 328 of the housing 312 from the annular rim 356. When in the first position, the forces generated by the compressed intermediate portion having the slots 352 may push the retainer 342 against the annular rim 356, preventing the retainer 312 from radially expanding.

During assembly of the vertebral anchor 310, the retainer 342 may be inserted into the lower opening 338 of the housing 312. For example, the plurality of alternating tabs 346 and slots 348 formed around the circumference of the retainer 342 may provide the retainer 342 with sufficient flexibility to be urged through the lower opening 338 from the lower end 330 of the housing 312 by radially compressing the retainer 342.

Figure 4B:
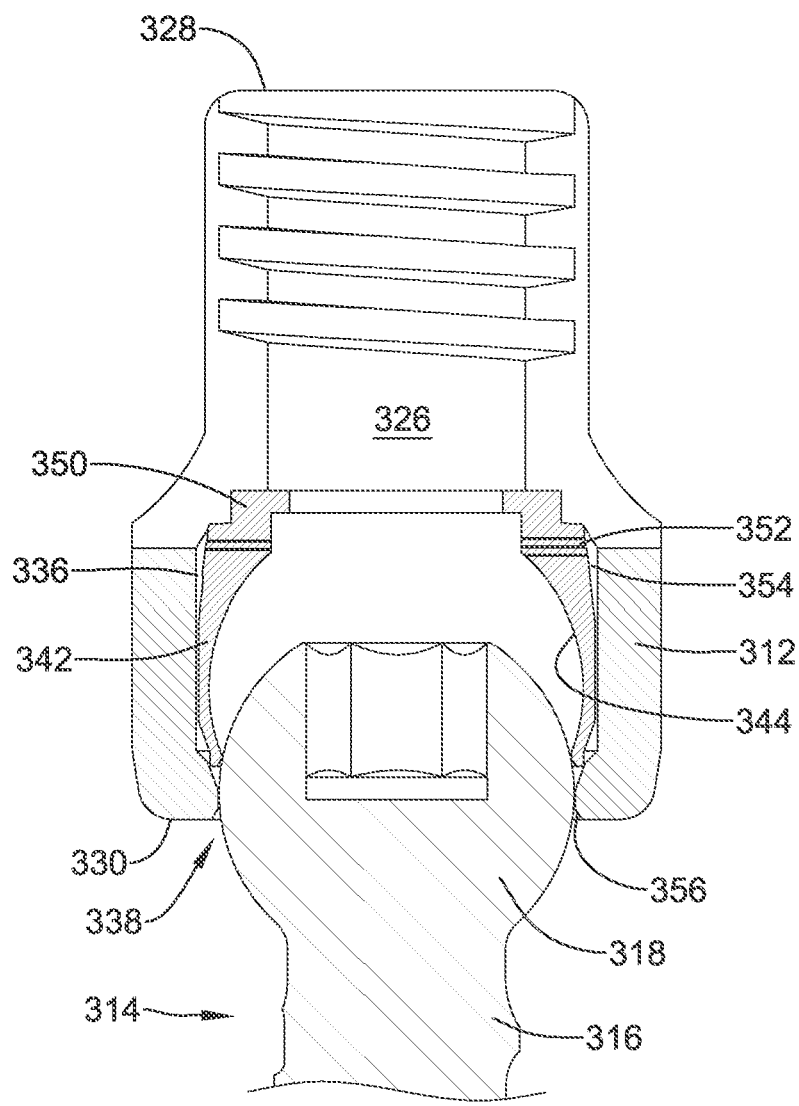
FIG. 4B is a cross-sectional view of the vertebral anchor of FIG. 4 while coupling the housing to the head portion of the bone screw.

With the retainer 342 positioned in the bore 326 of the housing 312, the head portion 318 of the bone screw 314 may be inserted into the cavity 344 of the retainer 342 through the lower opening 338 from the lower end 330 in a bottom loaded manner. The diameter of the head portion 318 of the bone screw 314 may be less than the diameter of the lower opening 338 at the annular rim 356 to allow the head portion 318 to pass therethrough. As shown in FIG. 4B, the head portion 318 of the bone screw 314, or another structure, may apply a force against the retainer 342 opposing and overcoming the biasing force of the intermediate portion having the slots 252 which urges the retainer 342 to the second position in which the retainer 342 is moved toward the upper end 328 of the housing 312 along the longitudinal axis of the bore 326. Now positioned in an enlarged diameter portion 336 of the bore 326 and radially unconstrained by the interior surface of the bore 326 and/or the annular rim 356 at the lower opening 338 of the housing 312, the flexibility of the retainer 342 allows the retainer 342 to be radially expanded. For example, the plurality of tabs 346 of the retainer 342 may be deflected radially outward in order to allow the head portion 318 of the bone screw 314 to pass into the cavity 344 of the retainer 342. The presence of the annular space 354 allows the retainer 342 to radially expand to accommodate, insertion of the head portion 318 into the cavity 344.

Once the head portion 318 of the bone screw 314 is positioned in the cavity 344, the applied force to the retainer 342 may be removed, allowing the biasing force of the intermediate portion having the slots 252 or other biasing means to move the retainer 342 back to the first position toward the lower end 330 of the housing 312 and into engagement with the reduced diameter annular portion of the housing 312 to prevent further radial expansion or splaying of the retainer 342. In some instances, the retainer 342 may include a lower beveled surface which contacts the annular rim 356 of the housing 312 to urge the tabs 346 of the retainer 342 radially inward and/or prevent radial splaying to secure the head portion 318 of the bone screw 314 in the cavity 344 of the retainer 342.

When an elongate member 340 is secured in the channel 320 of the housing 312, a clamping force may be exerted against the head portion 318 of the bone screw 314. However, because the lower opening of the retainer 342 when at the first position has a diameter less than the diameter of the head portion 318 of the bone screw 314, the head portion 318 is prevented from being removed from the cavity 344 of the retainer 342 since the annular rim 356 of the housing 312 resists radial expansion of the lower opening of the retainer 342 when pressed thereagainst.

Figure 5:
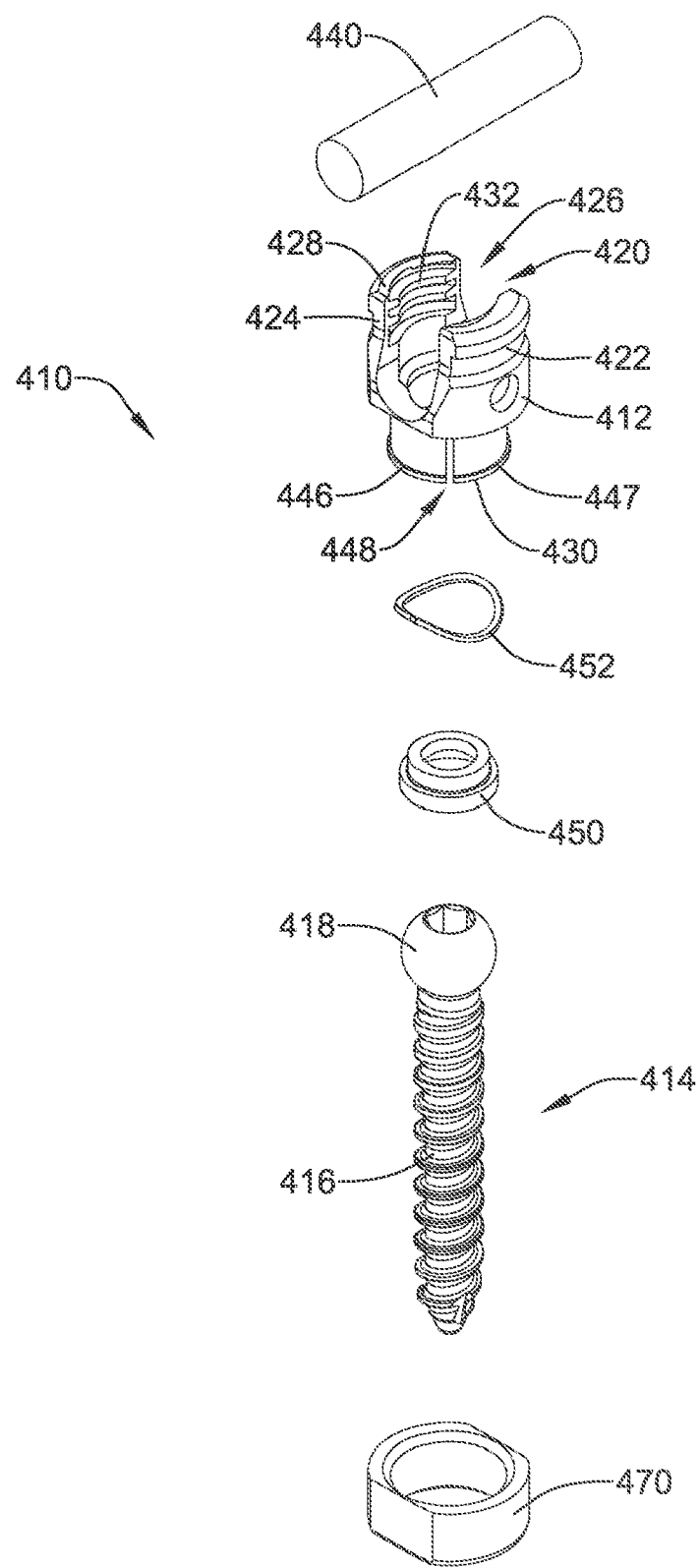
FIG. 5 is an exploded perspective view of components of yet another exemplary vertebral anchor.

Yet another exemplary embodiment of a vertebral anchor 410, shown as a polyaxial pedicle screw, is illustrated in FIG. 5. The vertebral anchor 410 may include several components. For example, the vertebral anchor 410 may include a housing 412 pivotably coupled to a bone screw 414. The bone screw 414 may include a shaft portion 416, which may in some instances be threaded, extending from a head portion 418, which may in some instances be spherically shaped. The shaft 416 may be configured to be installed into a bony region of a vertebra of the spinal column. For example, the shaft 416 may be installed into a pedicle of a vertebra, or other region of a vertebra. The bone screw 414 may be pivotable relative to the housing 412 such that the longitudinal axis of the bone screw 414 is positioned at one of multiple angular orientations relative to the longitudinal axis of the housing 412.

The housing 412 may include a channel 420, such as a U-shaped channel extending from one side of the housing 412 to an opposite second side of the housing 412. The channel 420 may be defined between opposing first and second legs 422, 424 of the housing 412. The housing 412 may also include a bore 426 extending through the housing 412 along a longitudinal axis from the upper end 428 to the lower end 430 of the housing 412 which intersects the channel 420.

The housing 412 of the vertebral anchor 410 may be configured to receive an elongate member 440 of a vertebral stabilization system, such as a rigid or flexible fixation element, including a spinal rod or flexible cord, therein. For example, the channel 420 may be open to the upper end 428 of the housing 412 such that the elongate member 440 may be positioned in the channel 420 in a top-loaded fashion in which the elongate member 440 is moved into the channel 420 of the housing 412 in a direction generally perpendicular to the longitudinal axis of the channel 420 of the housing 412.

The vertebral anchor 410 may also include a securing element, such as a threaded fastener (not shown) configured to rotatably engage the housing 412 to secure a portion of the elongate member 440 in the channel 420. For example, the threaded fastener may include threads which mate with a threaded portion 432 formed in the legs 422, 424 of the housing 412. In other embodiments, the fastener may include one or more flanges, cam surfaces, or other engagement features that engage with one or more channels, grooves, surfaces, or other engagement features of the housing 412 through rotation of the fastener. The fastener may be rotatably engaged between the spaced apart legs 422, 424 of the housing 412 which define the channel 420 therebetween.

The vertebral anchor 410 may also include one or more components for coupling the housing 412 to the head portion 418 of the bone screw 414. For instance, a lower portion of the housing 412 may include a cavity 444 for receiving the head portion 418 of the bone screw 414 therein. In some instances, the cavity 444 may be a spherically concave cavity complementing the spherical shape of the head portion 418 of the bone screw 414. The lower portion of the housing 412 may be formed of a resilient material, such as a pliable polymeric material or a malleable metallic material, providing the lower portion of the housing 412 a desired amount of flexibility. The lower portion of the housing 412 may include a plurality of alternating tabs 446 and slots 448 spaced around a periphery of the lower portion of the housing 412 enhancing the flexibility of the lower portion of the housing 412. For example, a radially inward force may be exerted on the tabs 146 to deflect the tabs 446 radially inward, whereas a radially outward force may be exerted on the tabs 446 to deflect or splay the tabs 446 radially outward to radially enlarge the lower opening 438 into the cavity 444 of the lower portion of the housing 412.

A collar 470 may be provided which may be positioned circumferentially around the tabs 446 of the lower portion of the housing 412 to prevent radial outward deflection or splaying of the tabs 446 when the housing 412 is coupled to the bone screw 414. In some instances, the collar 470 may include opposing flat or planar side surfaces to facilitate manipulation of the collar 470.

The vertebral anchor 410 may also include a spacer 450 positioned in the bore 426 having a first portion which is configured to engage an elongate stabilization member 440 disposed in the channel 420 of the housing 412 and a second portion which is configured to engage the head portion 418 of the bone screw 414.

The vertebral anchor 410 may further include a resilient spring means biasing the spacer 450 toward the lower end 430 of the housing 412 and into engagement with the head portion 418 of the bone screw 414. As shown in FIG. 5, the resilient spring means may be a wave washer 452, however, in other instances the resilient spring means may be a helical spring, elastomeric member, an integral portion of the spacer 450, or another structure configured to urge the spacer 450 toward the lower end 430 of the housing 412.

Figure 5A:
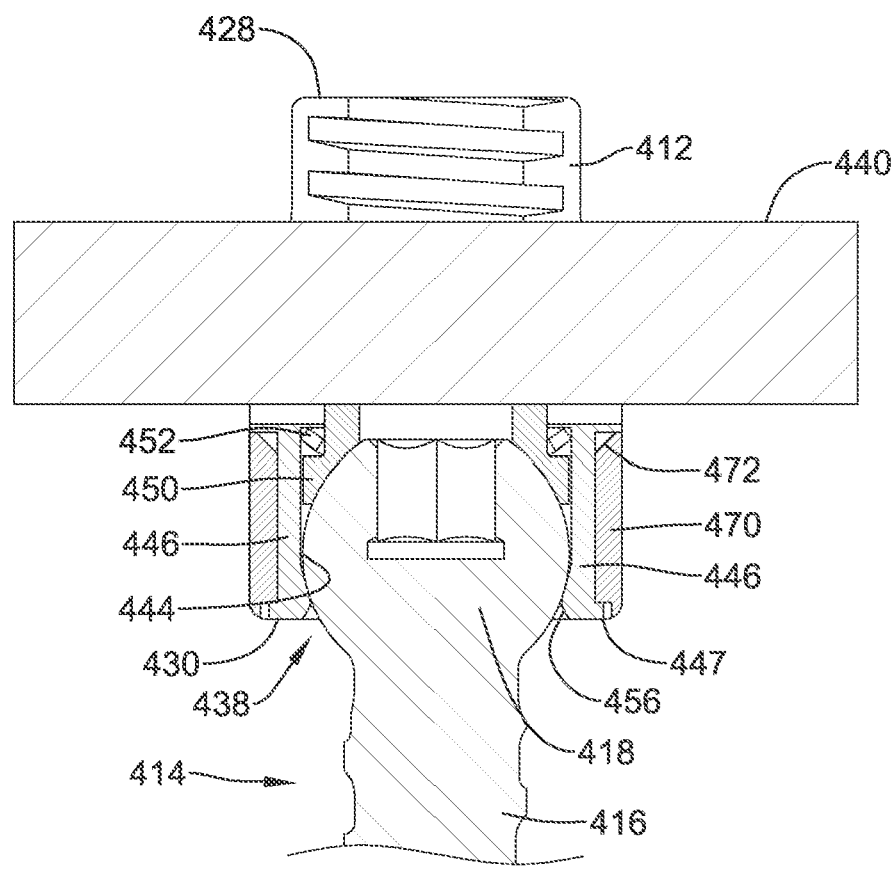
FIG. 5A is a cross-sectional view of the vertebral anchor of FIG. 5 with the housing coupled to the head portion of the bone screw.

The arrangement of components for coupling the housing 412 to the head portion 418 of the bone screw 414 is further illustrated in FIG. 5A. As shown in FIG. 5A, the head portion 418 of the bone screw 414 may be positioned in the cavity 444, surrounded by the tabs 446 of the housing 412. The spacer 450 may be positioned between the head portion 418 of the bone screw 414 and the elongate member 440, with a portion of the spacer 450 extending through the wave washer 452. The wave washer 452 may be positioned between the spacer 450 and the housing 412 and compressed between an annular rim of the housing 412 facing the lower end 430 of the housing 412 and an annular surface of an enlarged diameter portion of the spacer 450 facing the upper end 428 of the housing 412. The collar 470 may be positioned circumferentially around the tabs 446 of the lower portion of the housing 412, preventing radial outward deflection or splaying of the tabs 446.

Figure 5B:
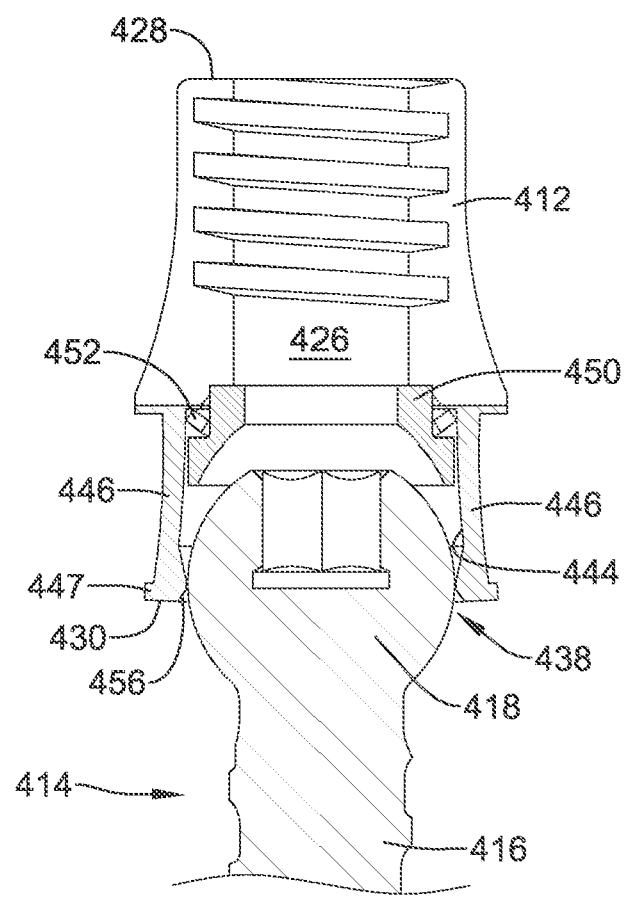
FIG. 5B is a cross-sectional view of the vertebral anchor of FIG. 5 while coupling the housing to the head portion of the bone screw.

During assembly of the vertebral anchor 10, the head portion 418 of the bone screw 412 may be passed into the cavity 444 of the lower portion of the housing 412 from the lower end 430 of the housing 412 by radially deflecting or splaying the plurality of tabs 446 radially outward from a first, equilibrium position to a second position in which the diameter of the annular rim 456 is greater than or equal to the diameter of the head portion 418, as shown in FIG. 5B.

Once the head portion 418 of the bone screw 414 is positioned in the cavity 444 above the annular rim 456, the tabs 446 will move back toward the first, equilibrium position with the annular rim 456 surrounding a portion of the head portion 418 below the greatest extent of the head portion 418. The collar 470 may then be positioned circumferentially around the tabs 446 of the lower portion of the housing 412, preventing further radial outward deflection or splaying of the tabs 446. In some instances, the collar 470 may include a beveled surface 472 proximate the upper opening of the collar 470 which facilitates advancing the collar 470 over the annular rim 447 of the tabs 446.

When an elongate member 440 is secured in the channel 420 of the housing 412, a clamping force may be exerted against the head portion 418 of the bone screw 414. However, the annular rim 456 of the housing 414, which has a diameter less than the diameter of the head portion 418 of the bone screw 414 when at the first position, prevents the head portion 418 from being removed from the cavity 444 since the collar 470 prevents radial slaying of the tabs 446.

Those skilled in the art will recognize that the present invention may be manifested in a variety of forms other than the specific embodiments described and contemplated herein. Accordingly, departure in form and detail may be made without departing from the scope and spirit of the present invention as described in the appended claims.

What is claimed is:
1. A spinal fusion system comprising:
one or more spinal stabilization structures;
a plurality of pedicle screws, each pedicle screw comprising:
  a fastener comprising:
    a threaded shaft; and
    a head connected to the threaded shaft; and
  a housing comprising:
    a lower component configured to receive the fastener in a bore extending along a longitudinal axis;

an upper component configured to receive a portion of one of the one or more spinal stabilization structures in a channel extending oblique to the longitudinal axis; and a spacer disposed within the upper component and the lower component to provide a buffer between the portion of the one of the one or more spinal stabilization structures in the upper component and the head of the fastener in the lower component;

wherein the lower housing component is positioned concentric with and radially outward of the spacer and the outer housing component is positioned concentric with and radially outward of the lower housing component; and a plurality of set screws, each configured to be received into a bore of one of the housings.

2. The spinal fusion system of claim 1, further comprising a flexible cord configured to be received into one or more of the housings.

3. The spinal fusion system of claim 1, wherein the one or more spinal stabilization structures comprises an elongate rod.

4. The spinal fusion system of claim 1, wherein:
an outer surface of the spacer comprises a cylindrical sidewall extending parallel to the longitudinal axis;
the bore of the lower component includes a cylindrical sidewall extending parallel to the longitudinal axis; and
the cylindrical sidewall of the spacer is configured to engage the cylindrical sidewall of the lower component to allow the spacer to rotate within in the bore about to the longitudinal axis.

5. The spinal fusion system of claim 1, wherein:
the upper component comprises a downward-facing annular ledge; and
the spacer comprises an upward-facing annular ledge configured to oppose the downward-facing annular ledge to facilitate retention of the spacer within the housing.

6. The spinal fusion system of claim 5, further comprising:
an annular planar surface within the housing upon which the portion of the one of the one or more spinal stabilization structures is configured to rest when the portion of the one of the one or more spinal stabilization structures is positioned in the channel;
wherein the annular planar surface is spaced apart from the upward-facing annular ledge.

7. The spinal fusion system of claim 6, wherein the annular planar surface is longitudinally displaced from the upward-facing annular ledge such that the annular planar surface is configured to extend into the channel and the upward-facing annular ledge is configured to be out of the channel when the spacer is positioned in the bore.

8. The spinal fusion system of claim 1, further comprising a ring positioned concentrically between the spacer and the upper component and that axially engages the upper component.

9. The spinal fusion system of claim 1, wherein:
the lower component is separate from and coupled to a lower end of the upper component such that an upward-facing surface of the lower component faces a downward-facing feature of the upper component; and
the spacer includes an upward-facing surface that faces the downward-facing feature of the upper component.

10. The spinal fusion system of claim 9, further comprising a ring positioned against the downward-facing feature of the upper component and the lower component and radially between the upper component and the spacer.

11. The spinal fusion system of claim 1, wherein the spacer is configured to attach to the head of the fastener.

12. The spinal fusion system of claim 11, further comprising:
a plurality of deflectable members coupled to the head portion of the bone screw to inhibit axial displacement of the bone screw out of the bore.

13. The spinal fusion system of claim 1, wherein the upper component and the lower component are arranged to permit relative rotation therebetween.

14. A spinal fusion system comprising:
a stabilization structure;
a first pedicle screw assembly configured to receive a first portion of the stabilization structure;
a first set screw configured to attach to the first pedicle screw assembly to secure the stabilization structure;
a second pedicle screw assembly comprising:
a fastener comprising:
a threaded shaft; and
a head connected to the threaded shaft; and
a housing comprising:
a lower component configured to receive the fastener in a bore extending along a longitudinal axis;
an upper component configured to receive a second portion of the stabilization structure in a channel extending oblique to the longitudinal axis; and
a spacer disposed within the upper component and the lower component to provide a buffer between the second portion of the stabilization structure in the upper component and the head of the fastener in the lower component, wherein the spacer comprises:
an upper portion comprising an annular planar surface within the housing upon which the stabilization structure is configured to rest; and
a lower portion held in engagement with the head of the fastener via coupling of at least two splayable members configured to hold the head of the fastener; and
a second set screw configured to be received into the upper component to secure the second portion of the stabilization structure in the channel.

15. The spinal fusion system of claim 14, wherein the spacer further buffers the second portion of the stabilization structure from engagement with a bottom of the channel.

16. The spinal fusion system of claim 14, wherein:
the upper component comprises a downward-facing annular ledge; and
the spacer comprises an upward-facing annular ledge configured to face the downward-facing annular ledge.

17. The spinal fusion system of claim 14, wherein:
an outer surface of the spacer comprises a cylindrical sidewall extending parallel to the longitudinal axis;
the bore of the lower component includes a cylindrical sidewall extending parallel to the longitudinal axis; and
the cylindrical sidewall of the spacer is configured to engage the cylindrical sidewall of the lower component to allow the spacer to translate in the bore parallel to the longitudinal axis.

18. The spinal fusion system of claim 14, wherein the stabilization structure comprises an elongate rod.

19. The spinal fusion system of claim 14, further comprising additional stabilization structures configured to be connected by the first pedicle screw assembly and the second pedicle screw assembly.

20. The spinal fusion system of claim 14, wherein the upper component and the lower component are arranged to permit relative rotation therebetween.

21. A spinal fusion system comprising:
- one or more spinal stabilization structures;
- a plurality of pedicle screws, each pedicle screw comprising:
  - a fastener comprising:
    - a threaded shaft; and
    - a head connected to the threaded shaft; and
  - a housing comprising:
    - a lower component configured to receive the fastener in a bore extending along a longitudinal axis;
    - an upper component configured to receive a portion of one of the one or more spinal stabilization structures in a channel extending oblique to the longitudinal axis; and
    - a spacer disposed within the upper component and the lower component to provide a buffer between the portion of the one of the one or more spinal stabilization structures in the upper component and the head of the fastener in the lower component;
  - wherein the spacer is configured to engage a head of a fastener within the lower housing component and the lower housing component is configured to provide a deflection limiter for the threaded shaft of the fastener; and
- a plurality of set screws, each configured to be received into a bore of one of the housings.

* * * * *

UNITED STATES PATENT AND TRADEMARK OFFICE
CERTIFICATE OF CORRECTION

PATENT NO. : 11,166,751 B2  
APPLICATION NO. : 17/248817  
DATED : November 9, 2021  
INVENTOR(S) : Shluzas et al.

Page 1 of 1

It is certified that error appears in the above-identified patent and that said Letters Patent is hereby corrected as shown below:

On the Title Page

Item (57), in "Abstract", in Column 2, Line 9, delete "lie" and insert --the-- therefor Signed and Sealed this  
Eighteenth Day of January, 2022

Drew Hirshfeld  
*Performing the Functions and Duties of the*  
*Under Secretary of Commerce for Intellectual Property and*  
*Director of the United States Patent and Trademark Office*